United States Patent
Voellmicke et al.

(10) Patent No.: US 9,895,236 B2
(45) Date of Patent: Feb. 20, 2018

(54) ENHANCED CAGE INSERTION ASSEMBLY

(71) Applicant: DePuy Synthes Products, Inc., Raynham, MA (US)

(72) Inventors: John C. Voellmicke, Franklin, MA (US); Michael J. O'Neil, West Barnstable, MA (US); Derek Shaw, North Attleboro, MA (US); Alexander Grinberg, Auburndale, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 97 days.

(21) Appl. No.: 15/147,544

(22) Filed: May 5, 2016

(65) Prior Publication Data
US 2016/0242929 A1    Aug. 25, 2016

Related U.S. Application Data

(63) Continuation of application No. 14/623,982, filed on Feb. 17, 2015, which is a continuation of application
(Continued)

(51) Int. Cl.
*A61B 17/58* (2006.01)
*A61B 17/60* (2006.01)
(Continued)

(52) U.S. Cl.
CPC ............ *A61F 2/4455* (2013.01); *A61F 2/447* (2013.01); *A61F 2/4601* (2013.01);
(Continued)

(58) Field of Classification Search
CPC ... A61B 17/88; A61B 17/885; A61B 17/8875; A61B 17/8894; A61B 2017/90
(Continued)

(56) References Cited

U.S. PATENT DOCUMENTS

| 1,802,560 A | 4/1931 | Kerwin et al. |
| 2,077,804 A | 4/1937 | Monroe et al. |

(Continued)

FOREIGN PATENT DOCUMENTS

| AU | 2005314079 | 10/2012 |
| CN | 1177918 | 4/1998 |

(Continued)

OTHER PUBLICATIONS

Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
(Continued)

*Primary Examiner* — Ellen C Hammond
*Assistant Examiner* — Christina Negrellirodrigue
(74) *Attorney, Agent, or Firm* — Baker & Hostetler LLP

(57) ABSTRACT

A method of delivering a fusion cage to an intervertebral disc space bounded by adjacent vertebral endplates, comprising the step of delivering the fusion cage into the disc space without contacting its teeth to the vertebral endplates during delivery, wherein a sheath is interposed between a cage surface and the endplates to prevent contact therebetween during delivery.

20 Claims, 12 Drawing Sheets

Related U.S. Application Data

No. 12/822,739, filed on Jun. 24, 2010, now Pat. No. 8,979,860.

(51) Int. Cl.

| | |
|---|---|
| *A61F 2/00* | (2006.01) |
| *A61F 2/44* | (2006.01) |
| *A61F 2/46* | (2006.01) |
| *A61F 2/30* | (2006.01) |

(52) U.S. Cl.
CPC ............ *A61F 2/4611* (2013.01); *A61F 2/446* (2013.01); *A61F 2/4465* (2013.01); *A61F 2002/30034* (2013.01); *A61F 2002/30092* (2013.01); *A61F 2002/30331* (2013.01); *A61F 2002/30604* (2013.01); *A61F 2002/30731* (2013.01); *A61F 2002/448* (2013.01); *A61F 2002/4475* (2013.01); *A61F 2310/00017* (2013.01); *A61F 2310/00023* (2013.01); *A61F 2310/00239* (2013.01)

(58) Field of Classification Search
USPC ............................ 606/90, 96, 99, 104, 86 A; 623/17.11–17.16
See application file for complete search history.

(56) References Cited

U.S. PATENT DOCUMENTS

| | | |
|---|---|---|
| 2,121,193 A | 6/1938 | Hanicke |
| 2,173,655 A | 9/1939 | Neracher et al. |
| 2,243,717 A | 5/1941 | Godoy et al. |
| 2,381,050 A | 8/1945 | Hardinge et al. |
| 2,388,056 A | 10/1945 | Hendricks et al. |
| 2,485,531 A | 10/1949 | William et al. |
| 2,489,870 A | 11/1949 | William et al. |
| 2,570,465 A | 10/1951 | Lundholm et al. |
| 2,677,369 A | 5/1954 | Knowles et al. |
| 3,115,804 A | 12/1963 | Lee et al. |
| 3,312,139 A | 4/1967 | Di et al. |
| 3,486,505 A | 12/1969 | Morrison et al. |
| 3,489,143 A | 1/1970 | Halloran et al. |
| 3,698,391 A | 10/1972 | Mahony et al. |
| 3,760,802 A | 9/1973 | Fischer et al. |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,867,728 A | 2/1975 | Stubstad et al. |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,175,555 A | 11/1979 | Herbert |
| 4,236,512 A | 12/1980 | Aginsky |
| 4,262,665 A | 4/1981 | Roalstad et al. |
| 4,275,717 A | 6/1981 | Bolesky |
| 4,312,353 A | 1/1982 | Shahbabian |
| 4,341,206 A | 7/1982 | Perrett et al. |
| 4,349,921 A | 9/1982 | Kuntz |
| 4,350,151 A | 9/1982 | Scott |
| 4,369,790 A | 1/1983 | McCarthy |
| 4,401,112 A | 8/1983 | Rezaian |
| 4,401,433 A | 8/1983 | Luther |
| 4,409,974 A | 10/1983 | Freedland |
| 4,449,532 A | 5/1984 | Storz |
| 4,451,256 A | 5/1984 | Weikl et al. |
| 4,456,005 A | 6/1984 | Lichty |
| 4,463,753 A | 8/1984 | Gustilo |
| 4,488,543 A | 12/1984 | Tornier |
| 4,494,535 A | 1/1985 | Haig |
| 4,532,660 A | 8/1985 | Field |
| 4,537,185 A | 8/1985 | Stednitz |
| 4,545,374 A | 10/1985 | Jacobson |
| 4,573,448 A | 3/1986 | Kambin |
| 4,601,710 A | 7/1986 | Moll |
| 4,625,725 A | 12/1986 | Davison et al. |
| 4,629,450 A | 12/1986 | Suzuki et al. |
| 4,632,101 A | 12/1986 | Freedland |
| 4,640,271 A | 2/1987 | Lower |
| 4,641,640 A | 2/1987 | Griggs |
| 4,653,489 A | 3/1987 | Tronzo |
| 4,667,663 A | 5/1987 | Miyata |
| 4,686,984 A | 8/1987 | Bonnet |
| 4,688,561 A | 8/1987 | Reese |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Tormala et al. |
| 4,759,766 A | 7/1988 | Buettner-Janz et al. |
| 4,760,843 A | 8/1988 | Fischer et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,858,601 A | 8/1989 | Glisson |
| 4,862,891 A | 9/1989 | Smith |
| 4,863,476 A | 9/1989 | Shepperd |
| 4,871,366 A | 10/1989 | von Recum et al. |
| 4,873,976 A | 10/1989 | Schreiber |
| 4,878,915 A | 11/1989 | Brantigan |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,959,064 A | 9/1990 | Engelhardt |
| 4,963,144 A | 10/1990 | Huene |
| 4,966,587 A | 10/1990 | Baumgart |
| 4,968,317 A | 11/1990 | Tormala et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 5,002,557 A | 3/1991 | Hasson |
| 5,011,484 A | 4/1991 | Breard |
| 5,013,315 A | 5/1991 | Barrows |
| 5,013,316 A | 5/1991 | Goble et al. |
| 5,059,193 A | 10/1991 | Kuslich |
| 5,062,849 A | 11/1991 | Schelhas |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,114,407 A | 5/1992 | Burbank |
| 5,116,336 A | 5/1992 | Frigg |
| 5,120,171 A | 6/1992 | Lasner |
| 5,122,133 A | 6/1992 | Evans |
| 5,122,141 A | 6/1992 | Simpson et al. |
| 5,123,926 A | 6/1992 | Pisharodi |
| 5,139,486 A | 8/1992 | Moss |
| 5,158,543 A | 10/1992 | Lazarus |
| 5,167,663 A | 12/1992 | Brumfield |
| 5,167,664 A | 12/1992 | Hodorek |
| 5,169,400 A | 12/1992 | Muhling et al. |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,697 A | 1/1993 | Hasson et al. |
| 5,178,501 A | 1/1993 | Carstairs |
| 5,183,464 A | 2/1993 | Dubrul et al. |
| 5,188,118 A | 2/1993 | Terwilliger |
| 5,195,506 A | 3/1993 | Hulfish |
| 5,201,742 A | 4/1993 | Hasson |
| 5,217,462 A | 6/1993 | Asnis et al. |
| 5,217,486 A | 6/1993 | Rice et al. |
| 5,224,952 A | 7/1993 | Deniega et al. |

(56) References Cited

U.S. PATENT DOCUMENTS

| | | |
|---|---|---|
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,246,441 A | 9/1993 | Ross et al. |
| 5,250,049 A | 10/1993 | Michael |
| 5,269,797 A | 12/1993 | Bonati et al. |
| 5,280,782 A | 1/1994 | Wilk |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,304,142 A | 4/1994 | Liebl et al. |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,324,261 A | 6/1994 | Amundson et al. |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,382,248 A | 1/1995 | Jacobson et al. |
| 5,387,213 A | 2/1995 | Breard et al. |
| 5,387,215 A | 2/1995 | Fisher |
| 5,390,683 A | 2/1995 | Pishardi |
| 5,395,317 A | 3/1995 | Kambin |
| 5,395,371 A | 3/1995 | Miller et al. |
| 5,401,269 A | 3/1995 | Buttner-Janz et al. |
| 5,407,430 A | 4/1995 | Peters |
| 5,415,661 A | 5/1995 | Holmes |
| 5,424,773 A | 6/1995 | Saito |
| 5,425,773 A | 6/1995 | Boyd et al. |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,790 A | 10/1995 | Dubrul |
| 5,464,427 A | 11/1995 | Curtis et al. |
| 5,470,333 A | 11/1995 | Ray |
| 5,472,426 A | 12/1995 | Bonati et al. |
| 5,474,539 A | 12/1995 | Costa et al. |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach, Jr. et al. |
| 5,505,710 A | 4/1996 | Dorsey, III |
| 5,507,816 A | 4/1996 | Bullivant |
| 5,512,037 A | 4/1996 | Russell et al. |
| 5,514,180 A | 5/1996 | Heggeness et al. |
| 5,520,690 A | 5/1996 | Errico et al. |
| 5,520,896 A | 5/1996 | de Graaf et al. |
| 5,522,899 A | 6/1996 | Michelson |
| 5,527,312 A | 6/1996 | Ray |
| 5,534,029 A | 7/1996 | Shima |
| 5,536,127 A | 7/1996 | Pennig |
| 5,540,688 A | 7/1996 | Navas |
| 5,540,693 A | 7/1996 | Fisher |
| 5,545,164 A | 8/1996 | Howland |
| 5,549,610 A | 8/1996 | Russell et al. |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble et al. |
| 5,562,738 A | 10/1996 | Boyd et al. |
| 5,564,926 A | 10/1996 | Brånemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,591,168 A | 1/1997 | Judet et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,639,276 A | 6/1997 | Weinstock et al. |
| 5,643,320 A | 7/1997 | Lower et al. |
| 5,645,589 A | 7/1997 | Li |
| 5,645,599 A | 7/1997 | Samani |
| 5,647,857 A | 7/1997 | Anderson et al. |
| 5,649,931 A | 7/1997 | Bryant et al. |
| 5,653,763 A | 8/1997 | Errico |
| 5,658,335 A | 8/1997 | Allen |
| 5,662,683 A | 9/1997 | Kay |
| 5,665,095 A | 9/1997 | Jacobson |
| 5,665,122 A | 9/1997 | Kambin |
| 5,667,508 A | 9/1997 | Errico et al. |
| 5,669,915 A | 9/1997 | Caspar et al. |
| 5,676,701 A | 10/1997 | Yuan et al. |
| 5,683,465 A | 11/1997 | Shinn et al. |
| 5,693,100 A | 12/1997 | Pisharodi |
| 5,697,977 A | 12/1997 | Pisharodi |
| 5,702,391 A | 12/1997 | Lin |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,541 A | 3/1998 | Anspach, III et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,282 A | 4/1998 | Anspach, III et al. |
| 5,743,881 A | 4/1998 | Demco |
| 5,743,912 A | 4/1998 | Lahille et al. |
| 5,743,914 A | 4/1998 | Skiba |
| 5,749,889 A | 5/1998 | Bacich et al. |
| 5,752,969 A | 5/1998 | Cunci et al. |
| 5,762,500 A | 6/1998 | Lazarof |
| 5,762,629 A | 6/1998 | Kambin |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,792,044 A | 8/1998 | Foley et al. |
| 5,797,909 A | 8/1998 | Michelson |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,836,948 A | 11/1998 | Zucherman et al. |
| 5,846,259 A | 12/1998 | Berthiaume |
| 5,849,004 A | 12/1998 | Bramlet |
| 5,851,216 A | 12/1998 | Allen |
| 5,860,973 A | 1/1999 | Michelson |
| 5,860,977 A | 1/1999 | Zucherman et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |

(56) References Cited

U.S. PATENT DOCUMENTS

| | | |
|---|---|---|
| 5,895,428 A | 4/1999 | Berry |
| 5,902,231 A | 5/1999 | Foley et al. |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Tormala et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,976,139 A | 11/1999 | Bramlet |
| 5,976,146 A | 11/1999 | Ogawa et al. |
| 5,976,186 A | 11/1999 | Bao et al. |
| 5,980,522 A | 11/1999 | Koros et al. |
| 5,984,927 A | 11/1999 | Wenstrom, Jr. et al. |
| 5,984,966 A | 11/1999 | Kiema et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,519 A | 12/1999 | Rosselli |
| 6,007,566 A | 12/1999 | Wenstrom, Jr. |
| 6,007,580 A | 12/1999 | Lehto et al. |
| 6,010,513 A | 1/2000 | Tormala et al. |
| 6,015,410 A | 1/2000 | Tormala et al. |
| 6,019,762 A | 2/2000 | Cole |
| 6,022,352 A | 2/2000 | Vandewalle |
| 6,030,162 A | 2/2000 | Huebner |
| 6,030,364 A | 2/2000 | Durgin et al. |
| 6,033,406 A | 3/2000 | Mathews |
| 6,036,701 A | 3/2000 | Rosenman |
| 6,039,761 A | 3/2000 | Li |
| 6,039,763 A | 3/2000 | Shelokov |
| 6,045,579 A | 4/2000 | Hochshuler |
| 6,048,309 A | 4/2000 | Flom et al. |
| 6,048,342 A | 4/2000 | Zucherman et al. |
| 6,053,935 A | 4/2000 | Brenneman et al. |
| 6,066,142 A | 5/2000 | Serbousek et al. |
| 6,068,630 A | 5/2000 | Zucherman et al. |
| 6,068,648 A | 5/2000 | Cole et al. |
| 6,074,390 A | 6/2000 | Zucherman et al. |
| 6,080,155 A | 6/2000 | Michelson |
| 6,080,193 A | 6/2000 | Hochshuler et al. |
| 6,083,244 A | 7/2000 | Lubbers et al. |
| 6,090,112 A | 7/2000 | Zucherman et al. |
| 6,096,038 A | 8/2000 | Micheson |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,113,637 A | 9/2000 | Gill et al. |
| 6,113,638 A | 9/2000 | Williams et al. |
| 6,117,174 A | 9/2000 | Nolan |
| 6,123,711 A | 9/2000 | Winters |
| 6,126,661 A | 10/2000 | Faccioli et al. |
| 6,126,663 A | 10/2000 | Hair |
| 6,127,597 A | 10/2000 | Beyar et al. |
| 6,129,762 A | 10/2000 | Li |
| 6,129,763 A | 10/2000 | Chauvin et al. |
| 6,146,384 A | 11/2000 | Lee et al. |
| 6,146,387 A | 11/2000 | Trott et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,161,350 A | 12/2000 | Espinosa |
| 6,162,234 A | 12/2000 | Freedland et al. |
| 6,162,236 A | 12/2000 | Osada |
| 6,168,595 B1 | 1/2001 | Durham et al. |
| 6,168,597 B1 | 1/2001 | Biedermann et al. |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,190,387 B1 | 2/2001 | Zucherman et al. |
| 6,193,757 B1 | 2/2001 | Foley et al. |
| 6,197,041 B1 | 3/2001 | Shichman et al. |
| 6,200,322 B1 | 3/2001 | Branch et al. |
| 6,206,826 B1 | 3/2001 | Mathews et al. |
| 6,206,922 B1 | 3/2001 | Zdeblick et al. |
| 6,213,957 B1 | 4/2001 | Milliman et al. |
| 6,217,509 B1 | 4/2001 | Foley et al. |
| 6,221,082 B1 | 4/2001 | Marino et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,238,397 B1 | 5/2001 | Zucherman et al. |
| 6,245,107 B1 | 6/2001 | Ferree |
| 6,248,108 B1 | 6/2001 | Tormala et al. |
| 6,251,111 B1 | 6/2001 | Barker et al. |
| 6,264,676 B1 | 7/2001 | Gellman et al. |
| 6,267,765 B1 | 7/2001 | Taylor et al. |
| 6,267,767 B1 | 7/2001 | Strobel et al. |
| 6,280,444 B1 | 8/2001 | Zucherman et al. |
| 6,287,313 B1 | 9/2001 | Sasso |
| 6,293,909 B1 | 9/2001 | Chu et al. |
| 6,293,952 B1 | 9/2001 | Brosens et al. |
| 6,296,647 B1 | 10/2001 | Robioneck et al. |
| 6,302,914 B1 | 10/2001 | Michelson |
| 6,306,136 B1 | 10/2001 | Baccelli |
| 6,319,254 B1 | 11/2001 | Giet et al. |
| 6,319,272 B1 | 11/2001 | Brenneman et al. |
| 6,332,882 B1 | 12/2001 | Zucherman et al. |
| 6,332,883 B1 | 12/2001 | Zucherman et al. |
| 6,332,895 B1 | 12/2001 | Suddaby |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,897 B1 | 4/2002 | Bonutti |
| 6,368,350 B1 | 4/2002 | Erickson et al. |
| 6,368,351 B1 | 4/2002 | Glenn |
| 6,371,971 B1 | 4/2002 | Tsugita et al. |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,379,363 B1 | 4/2002 | Herrington et al. |
| 6,387,130 B1 | 5/2002 | Stone |
| 6,409,766 B1 | 6/2002 | Brett |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,425,919 B1 | 7/2002 | Lambrecht |
| 6,428,541 B1 | 8/2002 | Boyd et al. |
| 6,428,556 B1 | 8/2002 | Chin |
| 6,436,140 B1 | 8/2002 | Liu et al. |
| 6,436,143 B1 | 8/2002 | Ross et al. |
| 6,440,154 B2 | 8/2002 | Gellman et al. |

(56) References Cited

U.S. PATENT DOCUMENTS

| | | |
|---|---|---|
| 6,440,169 B1 | 8/2002 | Elberg et al. |
| 6,443,989 B1 | 9/2002 | Jackson |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,468,277 B1 | 10/2002 | Justin et al. |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,488,710 B2 | 12/2002 | Besselink |
| 6,489,309 B1 | 12/2002 | Singh et al. |
| 6,491,714 B1 | 12/2002 | Bennett |
| 6,494,860 B2 | 12/2002 | Rocamora et al. |
| 6,494,893 B2 | 12/2002 | Dubrul et al. |
| 6,500,178 B2 | 12/2002 | Zucherman et al. |
| 6,506,192 B1 | 1/2003 | Gertzman et al. |
| 6,511,481 B2 | 1/2003 | Von Hoffmann et al. |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,527,774 B2 | 3/2003 | Lieberman |
| 6,527,803 B1 | 3/2003 | Crozet |
| 6,527,804 B1 | 3/2003 | Gauchet et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,554,831 B1 | 4/2003 | Rivard et al. |
| 6,554,852 B1 | 4/2003 | Oberlander |
| 6,558,389 B2 | 5/2003 | Clark et al. |
| 6,558,424 B2 | 5/2003 | Thalgott |
| 6,562,046 B2 | 5/2003 | Sasso |
| 6,562,049 B1 | 5/2003 | Norlander et al. |
| 6,562,074 B2 | 5/2003 | Gerbec et al. |
| 6,575,979 B1 | 6/2003 | Cragg |
| 6,576,016 B1 | 6/2003 | Hochshuler et al. |
| 6,579,293 B1 | 6/2003 | Chandran |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,595,998 B2 | 7/2003 | Johnson et al. |
| 6,596,008 B1 | 7/2003 | Kambin |
| 6,599,297 B1 | 7/2003 | Carlsson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,678 B2 | 9/2003 | Nishtala et al. |
| 6,620,196 B1 | 9/2003 | Trieu |
| 6,626,944 B1 | 9/2003 | Taylor |
| 6,632,224 B2 | 10/2003 | Cachia et al. |
| 6,635,059 B2 | 10/2003 | Randall et al. |
| 6,635,362 B2 | 10/2003 | Zheng |
| 6,641,564 B1 | 11/2003 | Kraus |
| 6,641,614 B1 | 11/2003 | Wagner et al. |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,655,962 B1 | 12/2003 | Kennard |
| 6,666,891 B2 | 12/2003 | Boehm, Jr. et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,664 B1 | 1/2004 | Al-Assir |
| 6,676,665 B2 | 1/2004 | Foley et al. |
| 6,679,833 B2 | 1/2004 | Smith et al. |
| 6,682,535 B2 | 1/2004 | Hoogland |
| 6,685,706 B2 | 2/2004 | Padget et al. |
| 6,685,742 B1 | 2/2004 | Jackson |
| 6,689,152 B2 | 2/2004 | Balceta et al. |
| 6,692,499 B2 | 2/2004 | Tormala et al. |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,760 B2 | 4/2004 | Dorchak et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,730,126 B2 | 5/2004 | Boehm, Jr. et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| 6,743,166 B2 | 6/2004 | Berci et al. |
| 6,743,255 B2 | 6/2004 | Ferree |
| 6,746,451 B2 | 6/2004 | Middleton et al. |
| 6,752,831 B2 | 6/2004 | Sybert et al. |
| 6,761,720 B1 | 7/2004 | Senegas |
| 6,770,075 B2 | 8/2004 | Howland |
| 6,773,460 B2 | 8/2004 | Jackson |
| 6,790,210 B1 | 9/2004 | Cragg et al. |
| 6,793,656 B1 | 9/2004 | Mathews |
| 6,793,678 B2 | 9/2004 | Hawkins |
| 6,796,983 B1 | 9/2004 | Zucherman et al. |
| 6,805,685 B2 | 10/2004 | Taylor |
| 6,805,695 B2 | 10/2004 | Keith et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,821,298 B1 | 11/2004 | Jackson |
| 6,824,565 B2 | 11/2004 | Muhanna |
| 6,830,589 B2 | 12/2004 | Erickson |
| 6,835,205 B2 | 12/2004 | Atkinson et al. |
| 6,835,206 B2 | 12/2004 | Jackson |
| 6,852,129 B2 | 2/2005 | Gerbec et al. |
| 6,855,167 B2 | 2/2005 | Shimp |
| 6,863,673 B2 | 3/2005 | Gerbec et al. |
| 6,875,215 B2 | 4/2005 | Taras et al. |
| 6,881,229 B2 | 4/2005 | Khandkar et al. |
| 6,887,243 B2 | 5/2005 | Culbert |
| 6,890,333 B2 | 5/2005 | von Hoffmann et al. |
| 6,893,464 B2 | 5/2005 | Kiester |
| 6,893,466 B2 | 5/2005 | Trieu |
| 6,902,566 B2 | 6/2005 | Zucherman et al. |
| 6,908,465 B2 | 6/2005 | von Hoffmann et al. |
| 6,916,323 B2 | 7/2005 | Kitchens |
| 6,921,403 B2 | 7/2005 | Cragg et al. |
| 6,923,811 B1 | 8/2005 | Carl et al. |
| 6,929,606 B2 | 8/2005 | Ritland |

(56) References Cited

U.S. PATENT DOCUMENTS

| | | |
|---|---|---|
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 6,972,035 B2 | 12/2005 | Michelson |
| 6,997,929 B2 | 2/2006 | Manzi et al. |
| 7,004,945 B2 | 2/2006 | Boyd et al. |
| 7,008,431 B2 | 3/2006 | Simonson |
| 7,018,412 B2 | 3/2006 | Ferreira et al. |
| 7,018,415 B1 | 3/2006 | McKay |
| 7,018,416 B1 | 3/2006 | Hanson et al. |
| 7,025,746 B2 | 4/2006 | Tal |
| 7,029,473 B2 | 4/2006 | Zucherman et al. |
| 7,037,339 B2 | 5/2006 | Houfburg et al. |
| 7,041,107 B2 | 5/2006 | Pohjonen et al. |
| 7,048,736 B2 | 5/2006 | Robinson et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,066,960 B1 | 6/2006 | Dickman |
| 7,066,961 B2 | 6/2006 | Michelson |
| 7,070,601 B2 | 7/2006 | Culbert et al. |
| 7,074,203 B1 | 7/2006 | Johanson et al. |
| 7,083,650 B2 | 8/2006 | Moskowitz et al. |
| 7,087,083 B2 | 8/2006 | Pasquet et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,118,572 B2 | 10/2006 | Bramlet et al. |
| 7,118,579 B2 | 10/2006 | Michelson |
| 7,118,598 B2 | 10/2006 | Michelson |
| 7,128,760 B2 | 10/2006 | Michelson |
| 7,153,305 B2 | 12/2006 | Johnson et al. |
| D536,096 S | 1/2007 | Hoogland et al. |
| 7,156,876 B2 | 1/2007 | Moumene et al. |
| 7,163,558 B2 | 1/2007 | Senegas et al. |
| 7,172,612 B2 | 2/2007 | Ishikawa |
| 7,179,294 B2 | 2/2007 | Eisermann et al. |
| 7,201,751 B2 | 4/2007 | Zucherman et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,238,204 B2 | 7/2007 | Le Couedic et al. |
| 7,267,683 B2 | 9/2007 | Sharkey et al. |
| 7,282,061 B2 | 10/2007 | Sharkey et al. |
| 7,300,440 B2 | 11/2007 | Zdeblick |
| 7,306,628 B2 | 12/2007 | Zucherman et al. |
| 7,309,357 B2 | 12/2007 | Kim |
| 7,326,211 B2 | 2/2008 | Padget et al. |
| 7,326,248 B2 | 2/2008 | Michelson |
| 7,335,203 B2 | 2/2008 | Winslow et al. |
| 7,361,140 B2 | 4/2008 | Ries et al. |
| 7,371,238 B2 | 5/2008 | Soboleski et al. |
| 7,377,942 B2 | 5/2008 | Berry |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,445,636 B2 | 11/2008 | Michelson |
| 7,445,637 B2 | 11/2008 | Taylor |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,488,326 B2 | 2/2009 | Elliott |
| 7,503,933 B2 | 3/2009 | Michelson |
| 7,507,241 B2 | 3/2009 | Levy et al. |
| 7,517,363 B2 | 3/2009 | Rogers |
| 7,520,888 B2 | 4/2009 | Trieu |
| 7,547,317 B2 | 6/2009 | Cragg |
| 7,556,629 B2 | 7/2009 | von Hoffmann et al. |
| 7,556,651 B2 | 7/2009 | Humphreys et al. |
| 7,569,054 B2 | 8/2009 | Michelson |
| 7,569,074 B2 | 8/2009 | Eiserman et al. |
| 7,588,574 B2 | 9/2009 | Assell et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,378 B2 | 12/2009 | Foley |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,691,120 B2 | 4/2010 | Shluzas et al. |
| 7,691,147 B2 | 4/2010 | Gutlin et al. |
| 7,699,878 B2 | 4/2010 | Pavlov et al. |
| 7,703,727 B2 | 4/2010 | Selness |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,740,633 B2 | 6/2010 | Assell et al. |
| 7,744,599 B2 | 6/2010 | Cragg |
| 7,749,270 B2 | 7/2010 | Peterman |
| 7,762,995 B2 | 7/2010 | Eversull et al. |
| 7,763,025 B2 | 7/2010 | Assell et al. |
| 7,763,055 B2 | 7/2010 | Foley |
| 7,766,930 B2 | 8/2010 | DiPoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,083 B2 | 9/2010 | Smith et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,832 B2 * | 3/2011 | Michelson ............ A61B 17/025 600/201 |
| 7,909,870 B2 | 3/2011 | Kraus |
| 7,922,729 B2 | 4/2011 | Michelson |

(56) References Cited

U.S. PATENT DOCUMENTS

| | | |
|---|---|---|
| 7,931,689 B2 | 4/2011 | Hochschuler et al. |
| 7,938,832 B2 | 5/2011 | Culbert et al. |
| 7,951,199 B2 | 5/2011 | Miller |
| 7,985,231 B2 | 7/2011 | Sankaran |
| 7,993,403 B2 | 8/2011 | Foley et al. |
| 7,998,176 B2 | 8/2011 | Culbert |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,105,382 B2 | 1/2012 | Olmos et al. |
| 8,109,977 B2 | 2/2012 | Culbert et al. |
| 8,114,088 B2 | 2/2012 | Miller |
| 8,133,232 B2 | 3/2012 | Levy et al. |
| 8,177,812 B2 | 5/2012 | Sankaran |
| 8,192,495 B2 | 6/2012 | Simpson et al. |
| 8,221,501 B2 | 7/2012 | Eiserman et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,273,128 B2 | 9/2012 | Oh et al. |
| 8,273,129 B2 | 9/2012 | Baynham et al. |
| 8,287,599 B2 | 10/2012 | McGuckin |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,366,777 B2 | 2/2013 | Matthis et al. |
| 8,382,842 B2 | 2/2013 | Greenhalgh et al. |
| 8,394,129 B2 | 3/2013 | Morgenstern Lopez et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Morgenstern et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,597,333 B2 | 12/2013 | Morgenstern Lopez et al. |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,728,160 B2 | 5/2014 | Globerman et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern Lopez et al. |
| 8,852,243 B2 | 10/2014 | Morgenstern Lopez et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum |
| 8,936,641 B2 | 1/2015 | Cain |
| 8,940,052 B2 | 1/2015 | Lechmann et al. |
| 8,979,860 B2 | 3/2015 | Voellmicke et al. |
| 9,039,771 B2 | 5/2015 | Glerum et al. |
| 9,091,488 B2 | 8/2015 | Malandain |
| 9,095,446 B2 | 8/2015 | Landry et al. |
| 9,095,447 B2 | 8/2015 | Barreiro et al. |
| 9,277,928 B2 | 3/2016 | Morgenstern Lopez |
| 2001/0012950 A1 | 8/2001 | Nishtala et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0049529 A1 | 12/2001 | Cachia et al. |
| 2001/0049530 A1 | 12/2001 | Culbert et al. |
| 2002/0001476 A1 | 1/2002 | Nagamine et al. |
| 2002/0010070 A1 | 1/2002 | Cales et al. |
| 2002/0032462 A1 | 3/2002 | Houser et al. |
| 2002/0055740 A1 | 5/2002 | Lieberman |
| 2002/0068976 A1 | 6/2002 | Jackson |
| 2002/0068977 A1 | 6/2002 | Jackson |
| 2002/0087152 A1 | 7/2002 | Mikus et al. |
| 2002/0091387 A1 | 7/2002 | Hoogland |
| 2002/0120335 A1 | 8/2002 | Angelucci et al. |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | von Hoffmann et al. |
| 2002/0151895 A1 | 10/2002 | Soboleski et al. |
| 2002/0151976 A1 | 10/2002 | Foley et al. |
| 2002/0161444 A1 | 10/2002 | Choi |
| 2002/0165612 A1 | 11/2002 | Gerber et al. |
| 2002/0183848 A1 | 12/2002 | Ray et al. |
| 2003/0004575 A1 | 1/2003 | Erickson |
| 2003/0004576 A1 | 1/2003 | Thalgott |
| 2003/0023305 A1 | 1/2003 | McKay |
| 2003/0028250 A1 | 2/2003 | Reiley et al. |
| 2003/0040799 A1 | 2/2003 | Boyd et al. |
| 2003/0063582 A1 | 4/2003 | Culbert |
| 2003/0065330 A1 | 4/2003 | Zucherman et al. |
| 2003/0065396 A1 | 4/2003 | Michelson |
| 2003/0069582 A1 | 4/2003 | Culbert et al. |
| 2003/0078667 A1 | 4/2003 | Manasas et al. |
| 2003/0083688 A1 | 5/2003 | Simonson |
| 2003/0130739 A1 | 7/2003 | Gerbec et al. |
| 2003/0135275 A1 | 7/2003 | Garcia |
| 2003/0139648 A1 | 7/2003 | Foley et al. |
| 2003/0139812 A1 | 7/2003 | Garcia |
| 2003/0139813 A1 | 7/2003 | Messerli et al. |
| 2003/0153874 A1 | 8/2003 | Tal |
| 2003/0187431 A1 | 10/2003 | Simonson |
| 2003/0204261 A1 | 10/2003 | Eiserman |
| 2003/0208122 A1 | 11/2003 | Melkent et al. |
| 2003/0208220 A1 | 11/2003 | Worley et al. |
| 2003/0220643 A1 | 11/2003 | Ferree |
| 2003/0229350 A1 | 12/2003 | Kay |
| 2003/0233102 A1 | 12/2003 | Nakamura et al. |
| 2003/0233145 A1 | 12/2003 | Landry et al. |
| 2004/0006391 A1 | 1/2004 | Reiley |
| 2004/0008949 A1 | 1/2004 | Liu et al. |
| 2004/0019359 A1 | 1/2004 | Worley et al. |
| 2004/0024463 A1 | 2/2004 | Thomas et al. |
| 2004/0030387 A1 | 2/2004 | Landry et al. |
| 2004/0049190 A1 | 3/2004 | Biedermann et al. |
| 2004/0049223 A1 | 3/2004 | Nishtala et al. |

(56) References Cited

U.S. PATENT DOCUMENTS

| | | |
|---|---|---|
| 2004/0054412 A1 | 3/2004 | Gerbec et al. |
| 2004/0059350 A1 | 3/2004 | Gordon et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0097924 A1 | 5/2004 | Lambrecht et al. |
| 2004/0097941 A1 | 5/2004 | Weiner et al. |
| 2004/0097973 A1 | 5/2004 | Loshakove et al. |
| 2004/0106925 A1 | 6/2004 | Culbert |
| 2004/0059339 A1 | 7/2004 | Roehm, III et al. |
| 2004/0127906 A1 | 7/2004 | Culbert et al. |
| 2004/0127991 A1 | 7/2004 | Ferree |
| 2004/0133280 A1 | 7/2004 | Trieu |
| 2004/0143284 A1 | 7/2004 | Chin |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0153065 A1 | 8/2004 | Lim |
| 2004/0153156 A1 | 8/2004 | Cohen et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0172133 A1 | 9/2004 | Gerber et al. |
| 2004/0186471 A1 | 9/2004 | Trieu |
| 2004/0186482 A1 | 9/2004 | Kolb et al. |
| 2004/0186570 A1 | 9/2004 | Rapp |
| 2004/0186577 A1 | 9/2004 | Ferree |
| 2004/0199162 A1 | 10/2004 | von Hoffmann et al. |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0225292 A1 | 11/2004 | Sasso et al. |
| 2004/0225361 A1 | 11/2004 | Glenn et al. |
| 2004/0230309 A1 | 11/2004 | DiMauro |
| 2004/0243239 A1 | 12/2004 | Taylor |
| 2004/0249466 A1 | 12/2004 | Liu et al. |
| 2004/0254575 A1 | 12/2004 | Obenchain et al. |
| 2004/0260297 A1 | 12/2004 | Padget et al. |
| 2004/0266257 A1 | 12/2004 | Ries et al. |
| 2005/0019365 A1 | 1/2005 | Frauchiger et al. |
| 2005/0033289 A1 | 2/2005 | Warren et al. |
| 2005/0033434 A1 | 2/2005 | Berry |
| 2005/0038515 A1 | 2/2005 | Kunzler |
| 2005/0043796 A1 | 2/2005 | Grant et al. |
| 2005/0065610 A1 | 3/2005 | Pisharodi |
| 2005/0090443 A1 | 4/2005 | Fallin et al. |
| 2005/0090833 A1 | 4/2005 | Di Poto |
| 2005/0102202 A1 | 5/2005 | Linden et al. |
| 2005/0113916 A1 | 5/2005 | Branch |
| 2005/0113917 A1 | 5/2005 | Chae et al. |
| 2005/0113927 A1 | 5/2005 | Malek |
| 2005/0118550 A1 | 6/2005 | Turri |
| 2005/0119657 A1 | 6/2005 | Goldsmith |
| 2005/0125062 A1 | 6/2005 | Biedermann et al. |
| 2005/0130929 A1 | 6/2005 | Boyd |
| 2005/0131406 A1 | 6/2005 | Reiley et al. |
| 2005/0131409 A1 | 6/2005 | Chervitz et al. |
| 2005/0131411 A1 | 6/2005 | Culbert et al. |
| 2005/0131538 A1 | 6/2005 | Chervitz et al. |
| 2005/0137595 A1 | 6/2005 | von Hoffmann et al. |
| 2005/0143734 A1 | 6/2005 | Cachia et al. |
| 2005/0149030 A1 | 7/2005 | Serhan |
| 2005/0154467 A1 | 7/2005 | Peterman et al. |
| 2005/0165398 A1 | 7/2005 | Reiley |
| 2005/0165485 A1 | 7/2005 | Trieu |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177240 A1 | 8/2005 | Blain |
| 2005/0182414 A1 | 8/2005 | Manzi et al. |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0203512 A1 | 9/2005 | Hawkins et al. |
| 2005/0216026 A1 | 9/2005 | Culbert |
| 2005/0222681 A1 | 10/2005 | Richley et al. |
| 2005/0251142 A1 | 11/2005 | von Hoffmann et al. |
| 2005/0256525 A1 | 11/2005 | Warren et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2005/0283238 A1 | 12/2005 | Reiley |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0020284 A1 | 1/2006 | Foley et al. |
| 2006/0030872 A1 | 2/2006 | Culbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041314 A1 | 2/2006 | Millard |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki |
| 2006/0079908 A1 | 4/2006 | Lieberman |
| 2006/0084977 A1 | 4/2006 | Lieberman |
| 2006/0084988 A1 | 4/2006 | Kim |
| 2006/0085010 A1 | 4/2006 | Lieberman |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0161166 A1 | 7/2006 | Johnson et al. |
| 2006/0178743 A1 | 8/2006 | Carter |
| 2006/0195103 A1 | 8/2006 | Padget et al. |
| 2006/0206207 A1 | 9/2006 | Dryer et al. |
| 2006/0217711 A1 | 9/2006 | Stevens et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235531 A1 | 10/2006 | Buettner |
| 2006/0247634 A1 | 11/2006 | Warner et al. |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2006/0276899 A1 | 12/2006 | Zipnick et al. |
| 2006/0276901 A1 | 12/2006 | Zipnick et al. |
| 2006/0276902 A1 | 12/2006 | Boyer, II et al. |
| 2006/0293662 A1 | 12/2006 | Boyer et al. |
| 2006/0293663 A1 | 12/2006 | Walkenhorst et al. |
| 2007/0010826 A1 | 1/2007 | Rhoda |
| 2007/0010886 A1 | 1/2007 | Banick et al. |
| 2007/0016191 A1 | 1/2007 | Culbert et al. |
| 2007/0032790 A1 | 2/2007 | Aschmann et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0073399 A1 | 3/2007 | Zipnick et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0149978 A1 | 6/2007 | Shezifi et al. |
| 2007/0162005 A1 | 7/2007 | Peterson et al. |
| 2007/0168036 A1 | 7/2007 | Ainsworth et al. |

(56) References Cited

U.S. PATENT DOCUMENTS

| | | |
|---|---|---|
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0191959 A1 | 8/2007 | Hartmann et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0219634 A1 | 9/2007 | Greenhalgh et al. |
| 2007/0233083 A1 | 10/2007 | Abdou |
| 2007/0233089 A1 | 10/2007 | DiPoto et al. |
| 2007/0233244 A1 | 10/2007 | Lopez et al. |
| 2007/0270954 A1 | 11/2007 | Wu |
| 2007/0270968 A1 | 11/2007 | Baynham et al. |
| 2007/0276375 A1 | 11/2007 | Rapp |
| 2007/0282449 A1 | 12/2007 | de Villiers et al. |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058598 A1 | 3/2008 | Ries et al. |
| 2008/0058944 A1 | 3/2008 | Duplessis et al. |
| 2008/0065219 A1 | 3/2008 | Dye |
| 2008/0077148 A1 | 3/2008 | Ries et al. |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0108996 A1 | 5/2008 | Padget et al. |
| 2008/0132934 A1 | 6/2008 | Reilly |
| 2008/0140207 A1 | 6/2008 | Olmos |
| 2008/0147193 A1 | 6/2008 | Matthis et al. |
| 2008/0154377 A1 | 6/2008 | Voellmicke et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0255618 A1 | 10/2008 | Fisher et al. |
| 2008/0262619 A1 | 10/2008 | Ray |
| 2008/0281425 A1 | 11/2008 | Thalgott |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2009/0005873 A1 | 1/2009 | Slivka et al. |
| 2009/0030423 A1 | 1/2009 | Puno |
| 2009/0054991 A1 | 2/2009 | Biyani |
| 2009/0069813 A1 | 3/2009 | von Hoffmann et al. |
| 2009/0076610 A1 | 3/2009 | Afzal |
| 2009/0099568 A1 | 4/2009 | Lowry et al. |
| 2009/0105712 A1 | 4/2009 | Dauster |
| 2009/0105745 A1 | 4/2009 | Culbert |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski |
| 2009/0177284 A1 | 7/2009 | Rogers et al. |
| 2009/0182429 A1 | 7/2009 | Humphreys et al. |
| 2009/0198339 A1 | 8/2009 | Kleiner |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0275890 A1 | 11/2009 | Leibowitz et al. |
| 2009/0292361 A1 | 11/2009 | Lopez et al. |
| 2010/0016905 A1 | 1/2010 | Greenhalgh et al. |
| 2010/0040332 A1 | 2/2010 | Van Den Meersschaut et al. |
| 2010/0076492 A1 | 3/2010 | Warner et al. |
| 2010/0076559 A1 | 3/2010 | Bagga |
| 2010/0082109 A1 | 4/2010 | Greenhalgh et al. |
| 2010/0114105 A1 | 5/2010 | Butters |
| 2010/0114147 A1 | 5/2010 | Biyani |
| 2010/0174314 A1 | 7/2010 | Mirkovic et al. |
| 2010/0179594 A1 | 7/2010 | Theofilos et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234956 A1 | 9/2010 | Attia et al. |
| 2010/0262240 A1 | 10/2010 | Chavatte et al. |
| 2010/0268231 A1 | 10/2010 | Kuslich et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0324607 A1 | 12/2010 | Davis |
| 2010/0331891 A1 | 12/2010 | Culbert et al. |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0054538 A1 | 3/2011 | Zehavi et al. |
| 2011/0071527 A1 | 3/2011 | Nelson et al. |
| 2011/0093074 A1 | 4/2011 | Glerum et al. |
| 2011/0098531 A1 | 4/2011 | To |
| 2011/0098628 A1 | 4/2011 | Yeung et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0153020 A1 | 6/2011 | Abdelgany et al. |
| 2011/0172716 A1 | 7/2011 | Glerum |
| 2011/0172774 A1 | 7/2011 | Varela |
| 2011/0238072 A1 | 9/2011 | Tyndall |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0215262 A1 | 8/2012 | Culbert et al. |
| 2012/0226357 A1 | 9/2012 | Varela |
| 2012/0232552 A1 | 9/2012 | Morgenstern et al. |
| 2012/0232658 A1 | 9/2012 | Morgenstern Lopez et al. |
| 2012/0265309 A1 | 10/2012 | Glerum et al. |
| 2012/0277795 A1 | 11/2012 | von Hoffmann et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0085572 A1 | 4/2013 | Glerum et al. |

(56) References Cited

U.S. PATENT DOCUMENTS

| | | |
|---|---|---|
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277204 A1 | 9/2014 | Sandhu |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0045894 A1 | 2/2015 | Hawkins et al. |
| 2015/0094610 A1 | 4/2015 | Morgenstern Lopez et al. |
| 2015/0094812 A1 | 4/2015 | Marden et al. |
| 2015/0094813 A1 | 4/2015 | Lechmann et al. |
| 2015/0112398 A1 | 4/2015 | Morgenstern Lopez et al. |
| 2015/0157470 A1 | 6/2015 | Voellmicke et al. |
| 2015/0173916 A1 | 6/2015 | Cain et al. |
| 2015/0216671 A1 | 8/2015 | Cain et al. |
| 2015/0216672 A1 | 8/2015 | Cain et al. |
| 2016/0045333 A1 | 2/2016 | Baynham |
| 2016/0317317 A1 | 11/2016 | Marchek et al. |
| 2016/0367265 A1 | 12/2016 | Morgenstern Lopez |

FOREIGN PATENT DOCUMENTS

| | | |
|---|---|---|
| CN | 101909548 A | 12/2010 |
| DE | 2804936 | 8/1979 |
| DE | 3023353 | 4/1981 |
| DE | 3911610 | 10/1990 |
| DE | 4012622 | 7/1997 |
| DE | 19832798 | 11/1999 |
| DE | 20101793 | 5/2001 |
| DE | 202008001079 | 3/2008 |
| EP | 077159 | 4/1983 |
| EP | 0260044 | 3/1988 |
| EP | 282161 | 9/1988 |
| EP | 0433717 | 6/1991 |
| EP | 0525352 | 2/1993 |
| EP | 0611557 | 8/1994 |
| EP | 0625336 | 11/1994 |
| EP | 678489 | 10/1995 |
| EP | 0270704 | 6/1998 |
| EP | 1046376 | 4/2000 |
| EP | 0853929 | 9/2002 |
| EP | 1290985 | 3/2003 |
| EP | 1378205 | 7/2003 |
| EP | 1374784 | 1/2004 |
| EP | 1532949 | 5/2005 |
| EP | 1541096 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 1845874 | 10/2012 |
| EP | 2764851 | 8/2014 |
| FR | 2649311 | 1/1991 |
| FR | 2699065 | 12/1992 |
| FR | 2728778 | 12/1994 |
| FR | 2718635 | 10/1995 |
| FR | 2745709 | 3/1996 |
| FR | 2730159 | 8/1996 |
| FR | 2800601 | 11/1999 |
| FR | 2801189 | 11/1999 |
| FR | 2808182 | 4/2000 |
| FR | 2874814 | 3/2006 |
| GB | 2157788 | 10/1985 |
| GB | 2173565 | 10/1986 |
| JP | 06-500039 | 6/1994 |
| JP | 06-319742 | 11/1994 |
| JP | 07-502419 | 3/1995 |
| JP | 07-184922 | 7/1995 |
| JP | 10-85232 | 4/1998 |
| JP | 11-89854 | 4/1999 |
| JP | 2003-010197 | 1/2003 |
| JP | 2003-126266 | 5/2003 |
| JP | 2003-526457 | 9/2003 |
| JP | 2006-516456 | 7/2006 |
| JP | 2007-54666 | 3/2007 |
| JP | 2011-509766 A | 3/2011 |
| JP | 2011-520580 | 7/2011 |
| JP | 4988203 | 7/2011 |
| JP | 5164571 | 8/2012 |
| JP | 64-52439 | 12/2012 |
| WO | WO 91/09572 | 12/1989 |
| WO | WO 93/04652 | 3/1993 |
| WO | WO 1994/004100 | 3/1994 |
| WO | WO 1995/031158 | 11/1995 |
| WO | WO 96/28100 | 9/1996 |
| WO | WO 97/00054 | 1/1997 |
| WO | WO 99/52478 | 10/1999 |
| WO | WO 1999/053871 | 10/1999 |
| WO | WO 99/62417 | 12/1999 |
| WO | WO 2000/012033 | 3/2000 |
| WO | WO 00/67652 | 5/2000 |
| WO | WO 00/76409 | 12/2000 |
| WO | WO 2000/074605 | 12/2000 |
| WO | WO 01/01895 | 1/2001 |
| WO | WO 2000/53127 | 1/2001 |
| WO | WO 2001001893 | 1/2001 |
| WO | WO 01/12054 | 2/2001 |
| WO | WO 2001/017464 | 3/2001 |
| WO | WO 01/80751 | 11/2001 |
| WO | WO 02/43601 | 6/2002 |
| WO | WO 03/21308 | 3/2003 |
| WO | WO 03/43488 | 5/2003 |
| WO | WO 2004/008949 | 1/2004 |
| WO | WO 2004/064603 | 8/2004 |
| WO | WO 2004/078220 | 9/2004 |
| WO | WO 2004/078221 | 9/2004 |
| WO | WO 2004/098453 | 11/2004 |
| WO | WO 2005/112834 | 12/2005 |
| WO | WO 2005/112835 | 12/2005 |
| WO | WO 2006/017507 | 2/2006 |
| WO | WO 2006/047587 | 5/2006 |
| WO | WO 2006/058281 | 6/2006 |
| WO | WO 2006/063083 | 6/2006 |
| WO | WO 2006/065419 | 6/2006 |
| WO | WO 2006/081843 | 8/2006 |
| WO | WO 2006/108067 | 10/2006 |
| WO | WO 2007/028098 | 3/2007 |
| WO | WO 2007/048012 | 4/2007 |
| WO | WO 2007/119212 | 10/2007 |
| WO | WO 2007/124130 | 4/2008 |
| WO | WO 2008/044057 | 4/2008 |
| WO | WO 2008/064842 | 6/2008 |

(56) References Cited

FOREIGN PATENT DOCUMENTS

| WO | WO 2008/070863 | 6/2008 |
|---|---|---|
| WO | WO 2007/009107 | 8/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2009/147527 | 12/2009 |
| WO | WO 2009/152919 | 12/2009 |
| WO | WO 2010/068725 | 6/2010 |
| WO | WO 2010/136170 | 12/2010 |
| WO | WO 2010/148112 | 12/2010 |
| WO | WO 2011/079910 | 7/2011 |
| WO | WO 2011/142761 | 11/2011 |
| WO | WO 2011/150350 | 12/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/062903 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |
| WO | WO 2014/144696 | 9/2014 |

OTHER PUBLICATIONS

Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
Hoogland, T. et al., Total Lumbar Intervertebral Disc Replacement: testing of a New Articulating Space in Human Cadaver Spines—24 1 Annual ORS, Dallas TX, Feb. 21-23, 1978, 8 pages.
*Spine Solutions Brochure—Prodisc 2001*, 16 pages.
Link SB Charite Brochure—Intervertebral Prosthesis 1988, 29 pages.
Alfen et al., "Developments in the Area of Endoscopic Spine Surgery", European Musculoskeletal Review 2006, pp. 23-24.
ThessysTM, Transforaminal Endoscopic Spine Systems, joi max Medical Solutions.
Brooks, M.D. et al., "Efficacy of Supplemental Posterior Transfacet Pedicle Device Fixation in the Setting of One- or Two-Level Anterior Lumbar Interbody Fusion", retrieved Jun. 19, 2017, 6 pages.
Brochure for PERPOS PLS System Surgical Technique by Interventional Spine, 2008, 8 pages.
Paul D. Fuchs, "The use of an interspinous implant in conjunction with a graded facetectomy procedure", Spine vol. 30, No. 11, pp. 1266-1272, 2005.
Iprenburg et al., "Transforaminal Endoscopic Surgery in Lumbar Disc Herniation in an Economic Crisis—The TESSYS Method", US Musculoskeletal, 2008, pp. 47-49.
King, M.D., Don, "Internal Fixation for Lumbosacral Fusion", The Journal of Bone and Joint Surgery, J. Bone Joint Surg Am., 1948; 30: 560-578.
Morgenstern R; "Transforaminal Endoscopic Stenosis Surgery—A Comparative Study of Laser and Reamed Foraminoplasty", in European Musculoskeletal Review, Issue 1, 2009.
ProMap TM EMG Navigation Probe. Technical Brochure Spineology Inc., Dated May 2009.
Chin, Kingsley R., M.D. "Early Results of the Triage Medical Percutaneous Transfacet Pedicular BONE-LOK Compression Device for Lumbar Fusion", accessed online Jul. 10, 2017, 10 pages.
Niosi, Christina A., "Biomechanical Characterization of the three-dimentinoal kinematic behavior of the Dynesys dynamic stabilization system: an in vitro study", Eur Spine J. (2006) 15: pp. 913-922.
Manal Siddiqui, "The Positional Magnetic Resonance Imaging Changes in the Lumbar Spine Following Insertion of a Novel Interspinous Process Distraction Device", Spine vol. 30, No. 23, pp. 2677-2682, 2005.
Vikram Talwar, "Insertion loads of the X STOP Interspinous Process Distraction System Designed to Treat Neurogenic Intermittent Claudication", Eur Spine J. (2006) 15: pp. 908-912.
James F. Zucherman, "A Multicenter, Prospective, Randomized Trial Evaluating the X STOP Interspinous Process Decompression System for the Treatment of Neurogenic Intermittent Claudication", Spine, vol. 30, No. 12, pp. 1351-1358, 2005.
Kambin et al., "Percutaneous Lateral Discectomy of the Lumbar Spine: A Preliminary Report"; Clin. Orthop.; 1983; 174: 127-132.
Medco Forum, "Percutaneous Lumbar Fixation Via PERPOS PLS System Interventional Spine", Sep. 2008, vol. 15, No. 37.
Medco Forum, "Percutaneous Lumbar Fixation via PERPOS System From Interventional Spine", Oct. 2007, vol. 14, No. 49.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.

* cited by examiner

ENHANCED CAGE INSERTION ASSEMBLY

CROSS-REFERENCE TO RELATED APPLICATIONS

This application is a continuation of and claims priority from U.S. Ser. No. 14/623,982, filed Feb. 17, 2015, which is a continuation of and claims priority from U.S. Ser. No. 12/822,739, filed Jun. 24, 2010, now U.S. Pat. No. 8,979,860, the specification of each of which is incorporated by reference in its entirety.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). These cytokines and MMPs help regulate the metabolism of the nucleus pulposus cells.

In some instances of degenerative disc disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of proinflammatory cytokines and/or MMPs that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing their water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices".

Designs of intervertebral fusion devices are generally either box-like (i.e., Smith-Robinson style) or threaded cylinders (i.e., Cloward style). Smith-Robinson style implants have the advantage of possessing better contact area to the vertebral endplates, but rely on a coarse surface texture (such as teeth) to prevent their migration once implanted. Insertion then requires over distraction of the disc space to slide the implant in or to provide a smoother implant, which can migrate post-op.

One such box-like design is the Brantigan cage, which is disclosed in U.S. Pat. No. 4,743,256 ("Brantigan"). Brantigan discloses an improved surgical method for eliminating spinal back pain caused by ruptured or degenerated vertebral discs by spanning the disc space between adjacent vertebrae with rigid fusion devices, or "cages", having surfaces facilitating bone ingrowth and bottomed on prepared sites of the vertebrae to integrate the implant with the vertebrae and to provide a permanent weight supporting strut maintaining the disc space.

One commercial box-like design is the injection-molded carbon fiber reinforced PEEK (CFRP) cage made by DePuy Spine. However, these cages are difficult to insert because of the interference fit that is required for intervertebral space distraction. In addition, the reinforced PEEK material that makes up the teeth is brittle and so is susceptible to breakage when applying impact or torque loads to the implant.

Current interbody devices are made from single materials (e.g., machined titanium, or molded and/or machined PEEK). Titanium has the disadvantage of being radiopaque (which can interfere with fusion assessment on x-ray) while also having a high modulus of elasticity (which can stress shield the bone graft). Injection molded CFRP is very brittle and susceptible to fracture during insertion. Unreinforced PEEK is much less brittle but also weaker than carbon-filled PEEK, requiring thicker-walled designs (diminishing space for bone graft). In addition, the teeth of an unreinforced PEEK cage are softer and so may allow more migration. Both PEEK and carbon-filled PEEK are radiolucent.

U.S. Pat. No. 6,824,565 ("Muhana") discloses implant and instrument designs wherein some of the implant embodiments have planked designs and a mating inserter instrument. However, the disclosed inserter wraps around the exterior of the implant and partially into grooves on the implant. Moreover, the disclosed implant is derived from bone and is not hollow. The insertion technique disclosed by Muhana requires a cutting tool to prepare a channel for the implant.

US Patent Publication 2008-0154377 (Voellmicke) discloses a cage adapted to contain an inserter within its inner volume during insertion.

US Patent Publication 2009-0198339 (Kleiner) discloses an implantable intervertebral fusion cage including a removable means for retaining material inside of the cage during implantation. Embodiments are directed toward an implantable intervertebral fusion cage that includes at least one removable shield or veneer that is capable of retaining a surgically useful material, such as a spinal fusion-inducing material, inside of the fusion cage during implantation and/or until the shield or veneer is removed. None of the Kleiner shields cover the teeth of the cages.

U.S. Pat. No. 7,569,054 (Michelson) discloses disc space docking and distraction means. In particular, Michelson discloses an apparatus for use in human surgery has a tubular member with a passage for providing protected access to a surgical site. The passage has a minimum width transverse to the mid-longitudinal axis of the tubular member. Two opposed extensions extend from the distal end of the tubular member. The extensions each have a length and a maximum height perpendicular to the length. The maximum height of the extensions are less than the length of each extension and greater than one-half the minimum width of the passage. Each extension has an interior surface at least in part facing the mid-longitudinal axis of the tubular member. The interior surfaces of the extensions are spaced apart from one another along the length of each extension a distance no less than the minimum width of the passage. Each extension has opposed bone contacting surfaces configured to contact portions of bone.

Other relevant instruments include those disclosed in U.S. Pat. No. 7,008,431 ("Simonson"); U.S. Pat. No. 5,797,909 ("Michelson II"); U.S. Pat. No. 6,080,155 ("Michelson III"); U.S. Pat. No. 6,096,038 ("Michelson IV"); U.S. Pat. No. 7,300,440 ("Zdeblick"); and U.S. Patent Publication 2009-0198339 ("Kleiner").

In summary, the insertion of both smooth and toothed intervertebral cages has proven to be problematic due to high resistance forces (friction) and interference fit of the cage and intervertebral space. Whereas toothed cages are difficult to insert, cages with smooth upper and lower surfaces have demonstrated undesirable migration.

Current injection-molded PEEK or carbon fiber reinforced PEEK (CFRP) cages are difficult to insert because of the interference fit between the textured/spiked surfaces of the implant and the bony endplates.

The difficulty of direct, unshielded cage insertion and final positioning in the disc space also increases the likelihood of bony endplate damage, as the disc space preparation, FSU distraction forces and insertion trajectory are variable.

Consistent and accurate placement of the posteriorly inserted spinal fusion cages is difficult because light tamping and impaction are employed for final positioning. Cages have been over inserted via pushing or impaction through the annulus and into the adjacent body cavities and/or structures.

Most cages are filled with graft and/or bone inducing substances including BMP and collagen sponge. It has been found that the graft and/or BMP frequently drips or falls out of the graft retaining pockets. The uncontrolled delivery of the BMP/graft can irritate adjacent tissues and prompt bone formation in undesired locations including heterotopic bone.

Many spinal fusion procedures require either pre and or post packing of the disc space, thereby increasing patient risk and operative time.

SUMMARY OF THE INVENTION

In accordance with the present invention, there is provided a cage insertion instrument adapted to insert an intervertebral interbody cage through a conventional spinal surgery approach (such as ALIF, TLIF, PLIF, or LLIF). In preferred embodiments, this instrument includes a cannulated sheath comprising a) a proximal cannulated portion, and b) a distal cannulated sheath that surrounds the cage during insertion into the disc space. The sheath shields the textured surface of the cage from the vertebral body endplates, thereby preventing their stress-inducing engagement therewith. The sheath has an expandable tapered or bulleted distal tip to ease insertion and placement of the instrument (and cage) within the disc space. Once the cage is inserted to its proper depth in the disc space, the sheath can be refracted while the cage is held stationary by a threaded rod disposed within the sheath. This retraction exposes the sharp, textured surface of the cage for engagement with the vertebral endplates.

Therefore, the inserter of the present invention provides a number of benefits to the spinal surgeon. In particular, it provides initial distraction of the disc space, improves the ease of insertion and placement of an intervertebral spacer, minimizes damage to the spacer and/or endplate during spacer insertion and placement, provides a means to deliver and contain graft within the spacer and surrounding disc space, and reduces the secondary positioning and time required to implant a spacer.

The sheath also provides a delivery and containment means for bone graft and/or BMP's, bone graft can be placed either within the cage, or distal or proximal to the cage for simultaneous delivery therewith. This containment means prevents leakage during insertion into the body, during placement into the disc space, and during final deployment into the disc space.

Therefore, in accordance with the present invention, there is provided an assembly comprising:

a) an intervertebral fusion cage having a leading end, a trailing end, an upper face and a lower face, and b) an inserter comprising:
 i) a cannulated rod holder having a bore therethrough,
 ii) a rod received within the bore of the cannulated rod holder, the rod adapted to mate with the cage,
 iii) a cannulated sheath receiving the cannulated rod holder, the sheath having a plurality of sheath portions extending distally therefrom, and wherein a first sheath portion has an inner portion bearing against the lower face of the cage, and wherein a second sheath portion has an inner portion bearing against the upper face of the cage.

The present invention includes a retractable sheath that holds a cage as it is inserted into the disc space, thereby shielding the sharp teeth of the cage from boney endplates and delivering graft to the disc space. Whereas conventional instrument systems that use delivery tubes for the cage do not place the tube into the disc space (but rather between the skin and the entrance to the disc space), the tubular sheath of the present invention enters the disc space.

The present invention also includes tubular, expandable spinal disc graft containment means.

Also in accordance with the present invention, there is provided a method of delivering a fusion cage to an intervertebral disc space bounded by adjacent vertebral endplates, comprising the step of:

a) delivering the fusion cage into the disc space without contacting its surfaces to the vertebral endplates during delivery.

In preferred embodiments thereof, a sheath is interposed between the cage surfaces and the endplates to prevent contact therebetween during delivery.

Also in accordance with the present invention, there is provided a method of delivering a fusion cage into the disc space, comprising the steps of:

a) inserting a distal end of a cannula into an intervertebral disc space, b) delivering the fusion cage through the cannula into the disc space.

DETAILED DESCRIPTION OF THE INVENTION

Figure 1A:
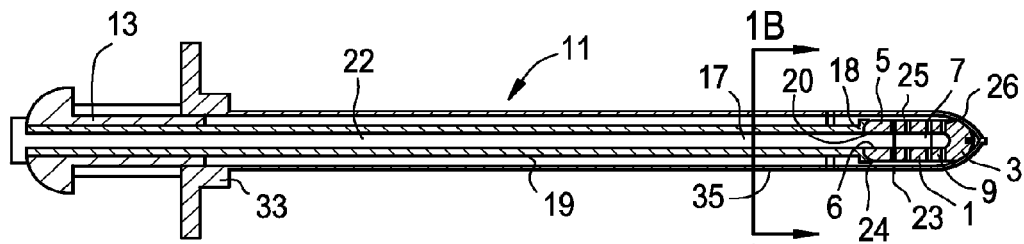
FIGS. 1A-1D disclose various views of an inserter of the present invention having four main components.
Figure 1B:
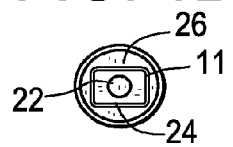
Figure 1C:
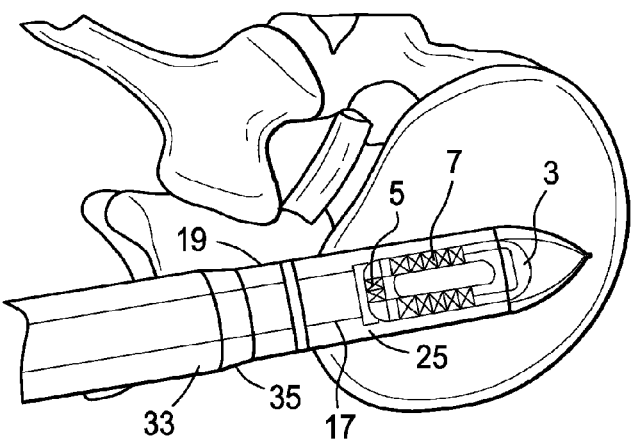
Figure 1D:
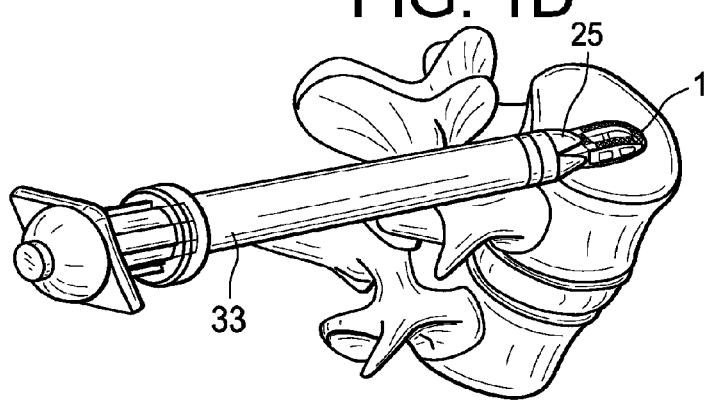

In some embodiments, the instrument comprises two, three, four or more components.

Now referring to FIGS. 1A-1D, there is provided an assembly of the present invention in which the inserter has four components: a sheath, a cannulated rod holder, a rod and a docking port. In particular, the assembly comprises:

a) an intervertebral fusion cage 1 having a leading end 3, a trailing end 5 having a threaded hole 6, an upper face 7 and a lower face 9, and b) an inserter 11 comprising:

i) a cannulated rod holder 13 having a bore therethrough and a distal end portion 17 having a distal end 18 bearing against the trailing end of the cage, ii) a rod 22 received within the bore of the cannulated rod holder, the rod having a threaded distal end 20 mating with the threaded hole of the cage, iii) a cannulated sheath 19 adapted to receive the cannulated rod holder, the sheath having a plurality of sheath portions 23,25 extending distally therefrom, iv) a docking port 33 having a bore therethrough and a substantially frustoconical distal end 35, wherein the cannulated sheath is slidingly received in the docking port and wherein a first sheath portion 23 has an inner portion 24 bearing against the lower face of the cage, and wherein a second sheath portion 25 has an inner portion 26 bearing against the upper face of the cage.

In general, the rod is a proximally-handled instrument that mates with the cage and typically has a distally extending screw thread similar to conventional posterior cage inserters. It is typically called a threaded securement rod. Typically, the rod has a threaded distal end, the trailing end of the cage has a mating threaded hole, and the threaded distal end of the rod is received in the mating threaded hole of the cage to secure the cage. The threaded connection allows the surgeon to keep the cage in its inserted position while the sheath is removed therefrom.

Figure 2:
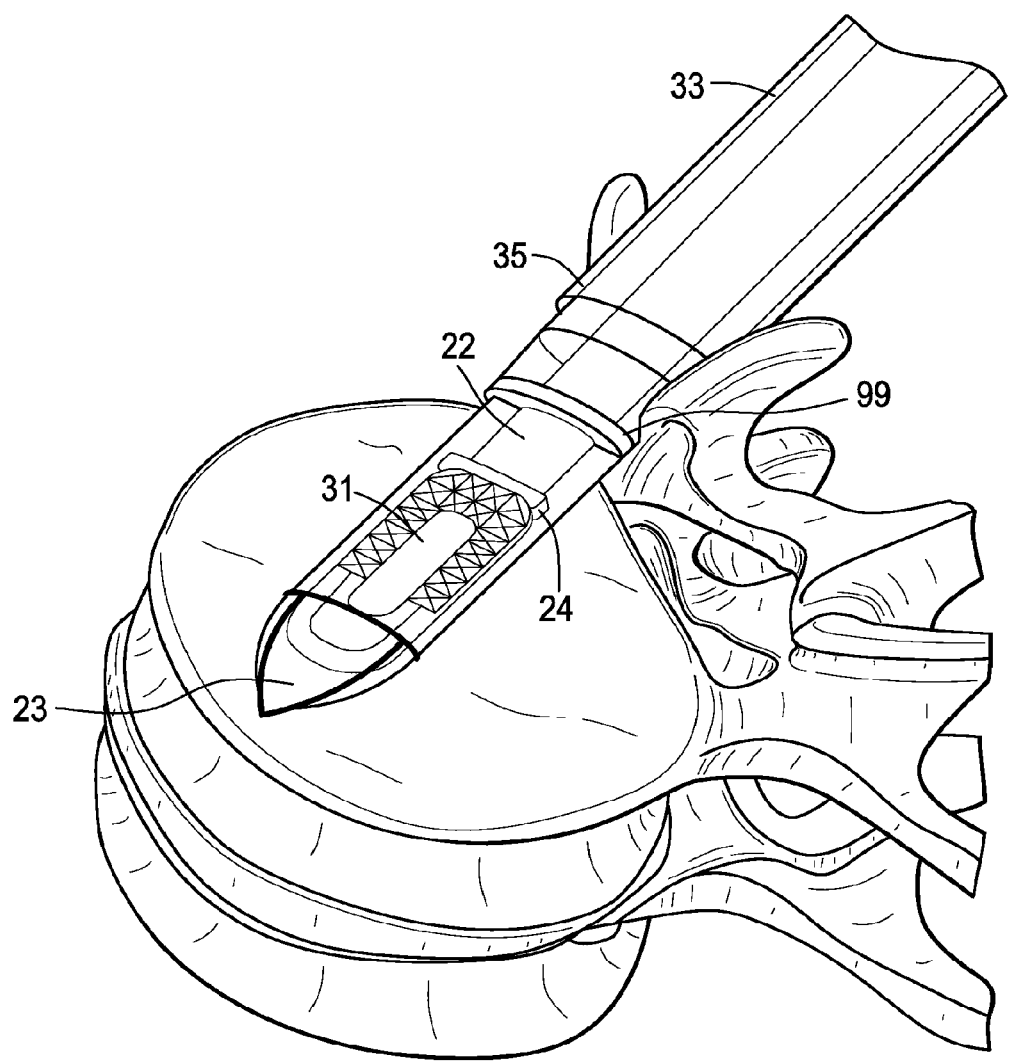
FIG. 2 discloses a fusion cage being held by an inserter of the present invention, along with the space available therein for graft placement.
Figure 3A:
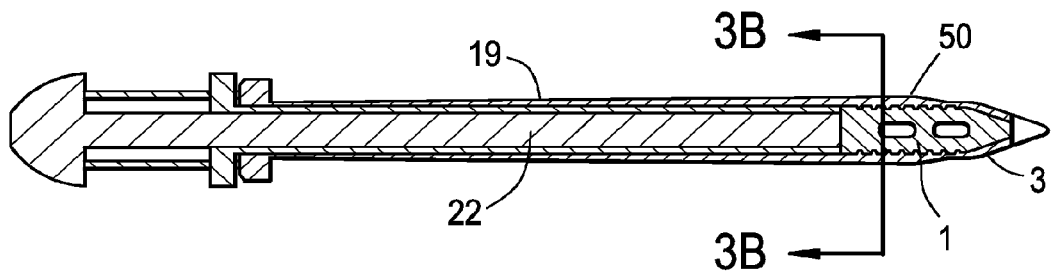
FIGS. 3A-3D disclose various views of an inserter of the present invention, wherein the sheath has a rectangular cross-section that tracks the cross-section of the fusion cage.
Figure 3B:
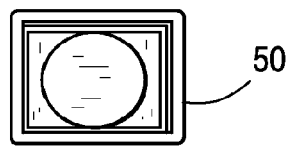
Figure 3C:
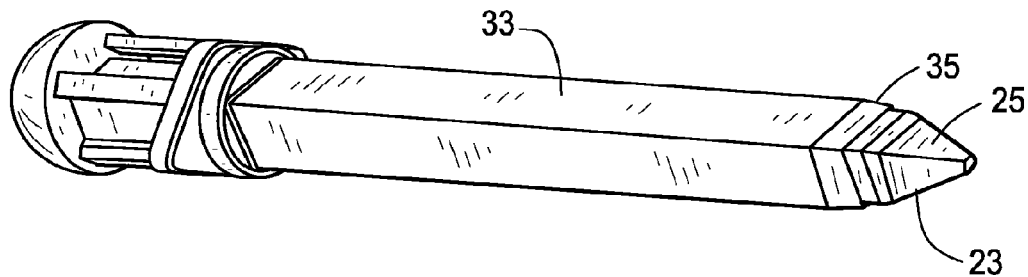
Figure 3D:
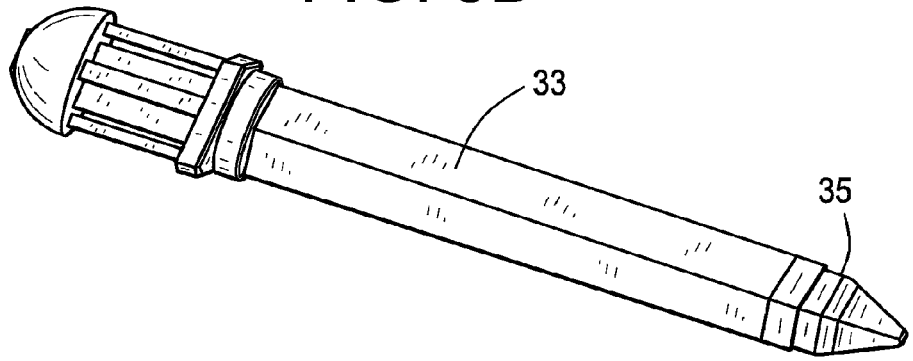
Figure 4A:
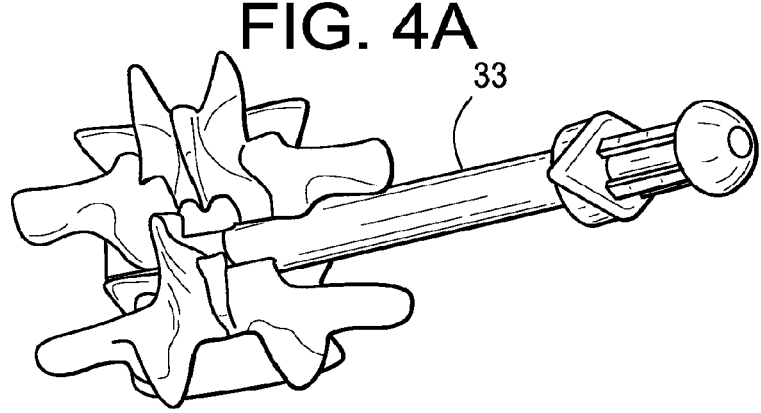
FIGS. 4A-4D disclose various steps by which the inserter of FIGS. 3A-3D inserts a cage into a disc space.
Figure 4B:
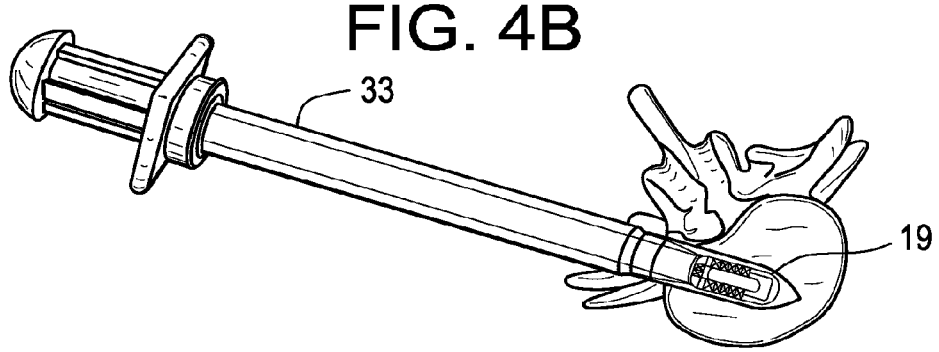
Figure 4C:
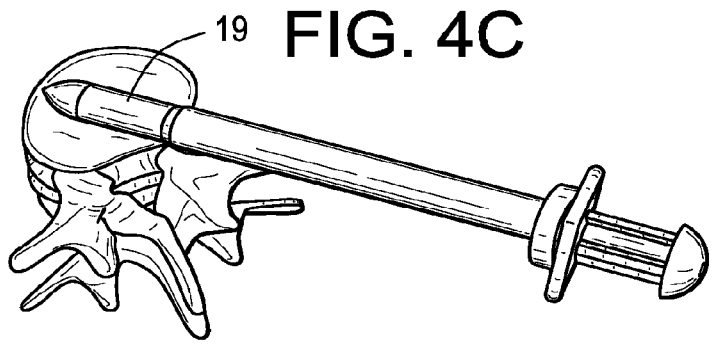
Figure 4D:
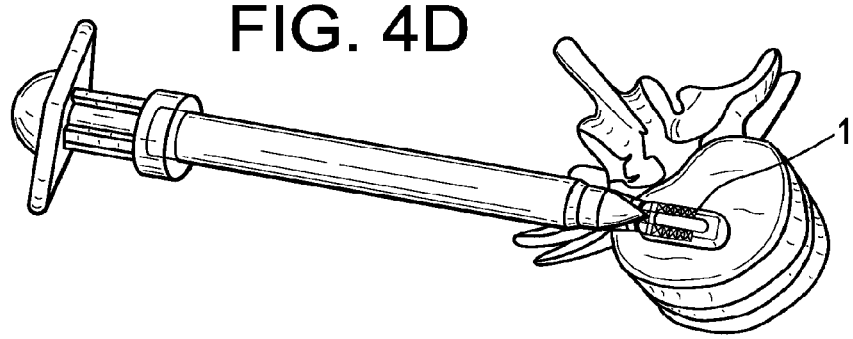

The function of the cannulated rod holder is to hold cage in position as sheath is retracted. As shown in FIG. 2, it typically has distally extending feet 24 for bearing against the trailing end of the cage. Thus, in some embodiments, the cannulated rod holder may be considered a cannulated cage holder as well. In some embodiments, the cannulated rod holder can further include a cylindrical flange or "piston" 99 that extends radially about the distal portion of the rod. This piston allows for sealed graft or BMP delivery distally thereof. As shown in FIG. 2, graft materials 31 can be placed within the cage, or placed distal and/or proximal to the cage within the cage holder, thereby eliminating the need to pre-pack or post-pack the disc space with graft materials. The piston feature provides a proximal stop for such graft placement proximal of the cage.

Referring back to FIGS. 1A-1D, the bulleted sheath 19 is a retractable cannulated sheath that slides over the rod/rod holder assembly. The sheath preferably has a very smooth (i.e., low coefficient of friction), semi-rigid inner wall 24,26 with a wall thickness of approximately 0.5 mm or less. Preferred materials of construction for the sheath include: polymerics (such as polyethylene, polypropylene, PEEK, polyurethane, and PTFE) or metallics (such as stainless steel, titanium alloy, and nitinol). One preferred sheath is constructed of a radiolucent material that allows for fluoroscopic imaging of the cage. In some embodiments, the sheath has a bulleted distal tip that optionally possesses at least one expansion slot (with four such slots shown in FIGS. 1A-1D, 2 and 4A-4D). Now referring to FIGS. 3A-3D, in some embodiments, the sheath can be produced in varying shapes, including those having a rectangular transverse cross-section 50.

In use, and now referring to FIG. 2, the sheath typically contains bone graft 31. In some cases, at least a portion of the bone graft is located within the cage. In others, at least a portion of the bone graft is located outside of the cage.

In some embodiments, the sheath comprises a distal pair of cup-like, opposed sheath half leafs, while in others the sheath comprises four sheath quarter leafs. Now referring to FIGS. 6A-6B, the proximal portion 98 of each distal sheath leaf 23, 25 is adapted to flex, thereby allowing the distal tip of the distal sheath leaf to open and close. In preferred embodiments, in their collapsed arrangement, the distal sheath leaves form a substantially conical shape distally, thereby forming a distal bullet tip. In other cases, the distal sheath leaves form a substantially tubular sheath shape proximally. In this way, the collective shape of the distal sheath leaves is much like that of a bulleted cage—i.e., it has a tubular body and a bulleted distal tip.

The distal sheath portions can also possess smooth outer surfaces to reduce friction and thereby increase the ease of insertion.

Typically, and now referring to FIG. 3A-3D, the inserter further comprises: iv) a docking port 33 having a bore therethrough and a substantially frustoconical distal end 35, wherein the cannulated sheath is slidingly received in the docking port. The docking port acts as a refractor for soft tissue and helps to place the cannulated sheath upon the vertebral body or within the disc. The docking port can also control insertion angle and depth of the bulleted sheath with enclosed cage. In some embodiments, the port is a cannulated body having a throughbore and a distal end portion having a tapered, cannulated, pyramidal or frustoconical shape.

The present invention is believed to be compatible with any conventional fusion cage. Typically, the upper and lower faces of the cage comprise a plurality of teeth. In some embodiments, the cage has a substantially rectangular transverse cross-section and the sheath has a corresponding substantially rectangular transverse cross-section. In some embodiments, the cage has a substantially circular transverse cross-section and the sheath has a corresponding substantially circular transverse cross-section. In some embodiments, the cage has a substantially elliptical transverse cross-section and the sheath has a corresponding substantially elliptical transverse cross-section.

Typically, the cage distracts the disc space during insertion. It is easy to insert and optimizes clinical performance once in place because it resists migration and subsidence, has an appropriate stiffness for load sharing, is preferably radiolucent, and has a shape that is able to contain injected graft material such as growth factors. In addition, the cage is robust over a wide variation of surgical technique because it will not break even when large forces are applied thereto.

The cage of the present invention is preferably compatible with the broad use of injectable paste-like bone grafting materials, such as BMP-containing pastes. It may be inserted empty and then filled with graft in-situ. With the availability of injectable pastes, cages will no longer require large, contiguous internal volumes to accept morselized/granular bone graft. Spaces can be smaller and more numerous. The cage of the present invention will be contained and shielded by the bulleted sheath and will therefore not experience as large impact loads during insertion.

Now referring to FIGS. 3A-3D, in some embodiments, the cage has a transverse cross-section 50 that is rectangular, and the transverse cross sections of the port, the bulleted sheath and the cannulated cage holder can substantially match that of the cage itself. This is a preferred embodiment, as it minimizes the over-distraction required in other embodiments for cage insertion.

Now referring to FIGS. 4A-4D, in one method of using the four-component inserter with the present invention, the sequence of implantation steps are as follows:

(1) fill the cage and sheath with bone graft.
(2) dock the docking port 33 onto the disc space. The port can be used to direct the angle and location of any desired disc clearing effort as well as cage implantation.
(3) advance of the bulleted sheath. The bulleted sheath 19 containing the graft and cage are advanced to the desired depth and location. The bulleted sheath reduces insertion forces due to its shape and its lubricious material of construction, while encasing the cage and its associated securement features (teeth).
(4) imaging. Imaging is performed to confirm cage positioning.
(5) sheath refraction: The sheath is retracted from the cage 1, thereby exposing the cage and its contents to the vertebral endplates.
(6) Cage Disconnection/Release: Following retraction of the sheath, the threaded rod is disengaged from the cage, thereby leaving the cage in the disc space at the desired location.
(7) Added Graft Injection (optional): As a last step, additional graft can be deployed via packing or injecting through the cannulated cage holder.

Figure 5:
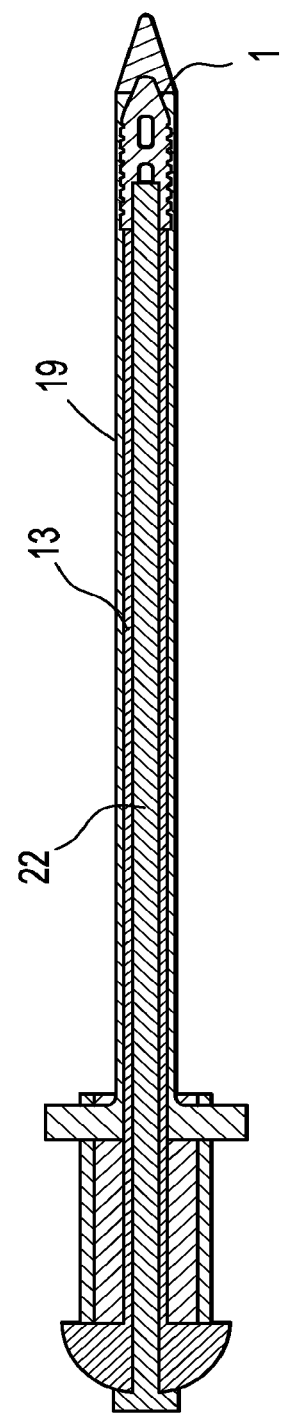
FIG. 5 discloses an inserter of the present invention having three main components.

Now referring to FIG. 5, in some embodiments, the inserter instrument of the present invention is a three-component design that does not have a docking port. This design includes:

a) a threaded securement rod 23 that mates with the cage via screw threads in a manner similar to conventional posterior cage inserters;

b) a cannulated cage holder 13 to receive the rod and hold the cage in position as the sheath is retracted; and c) a bulleted cannulated sheath 19.

In using the inserter of FIG. 5, the bulleted sheath (containing the graft and the cage 1) is advanced to the desired location. Due to the shape and lubricious material which encases the cage and associated securement features (such as teeth), the bulleted sheath reduces insertion forces. Imaging is then performed to confirm positioning.

Figure 6A:
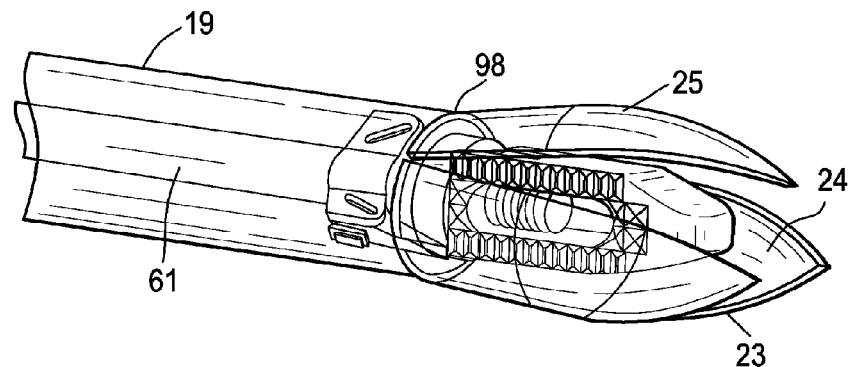
FIGS. 6A-6B discloses an inserter of the present invention having two main components.
Figure 6B:
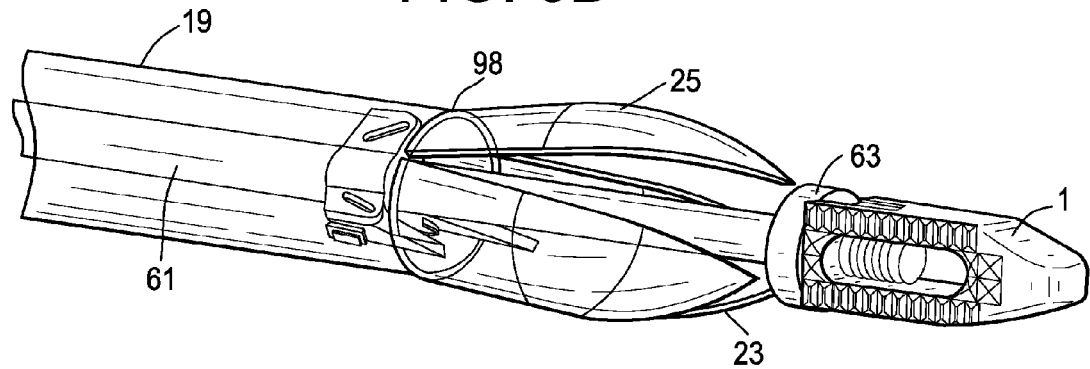

Now referring to FIGS. 6A-6B, there is provided a simple two-component embodiment of the present invention employing a cage pusher/holder 61 and an insertion sheath 19. The cage pusher/holder features the threaded feature of the rod and the shoulder 63 of the cannulated rod holder of FIGS. 1A-1D. The cage pusher/holder holds the cage 1 in position as sheath is retracted, and the feet can act as a piston for sealed graft delivery. The bulleted sheath 19 (containing the graft and cage) is advanced to the desired location. The bulleted sheath reduces insertion forces due to the shape and lubricious material which encases the cage and associated securement features (such as teeth). Imaging is performed to confirm positioning.

Figure 7A:
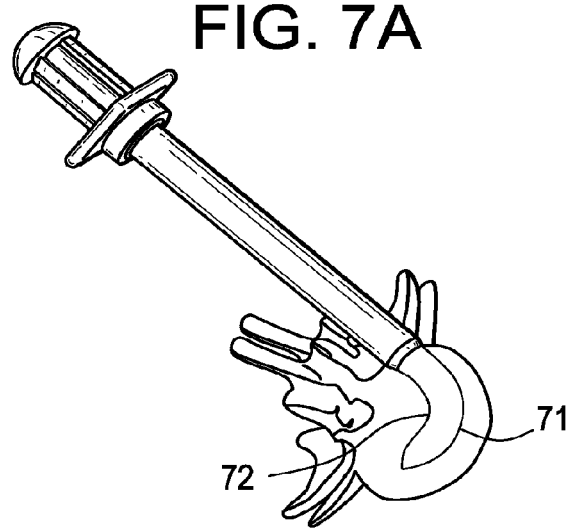
FIGS. 7A-7B discloses an inserter of the present invention having a curved distal sheath.
Figure 7B:
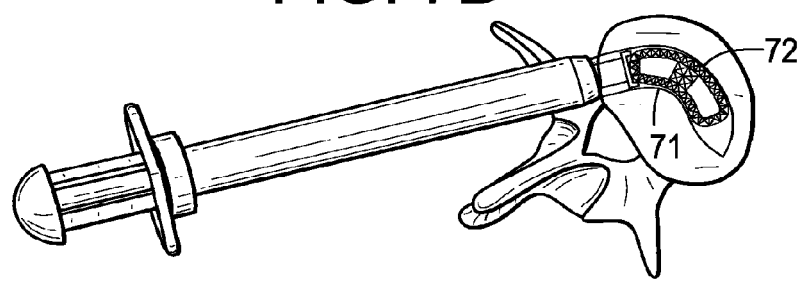

In some embodiments, and now referring to FIGS. 7A and 7B, the cages of the assembly of the present invention have curved sidewalls. Typically, these curved cages are placed in an anterior portion of the disc space. The curved sheath reduced the need for post-insertion manipulation of theses cages with conventional insertion methods which is more challenging due to the final position of the cage and the increased manipulation and forces that are required to push it in.

Figure 7C:
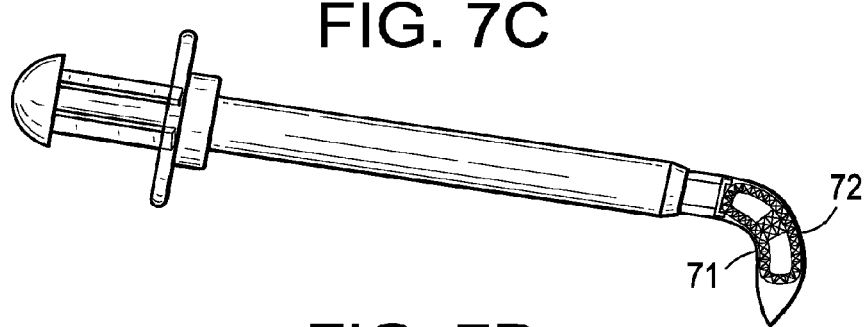
FIGS. 7C-7D discloses the distal and proximal loading of the inserter of FIGS. 7A-7B.
Figure 7D:
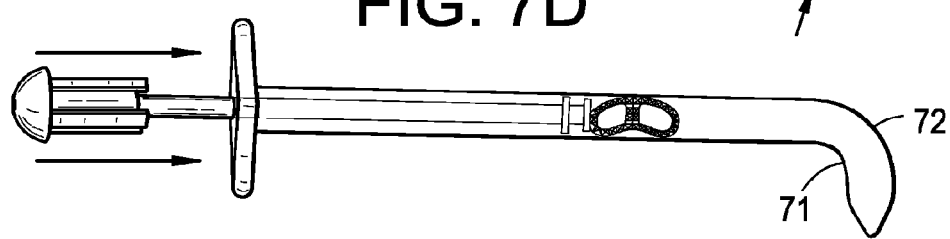
Figure 8A:
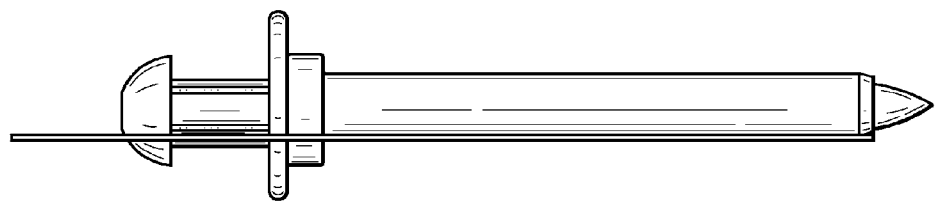
FIGS. 8A-8D disclose the sequential advance of the curved distal sheath of an inserter of the present invention.
Figure 8B:
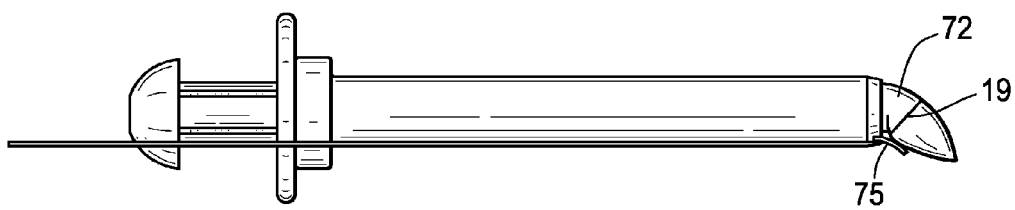
Figure 8C:
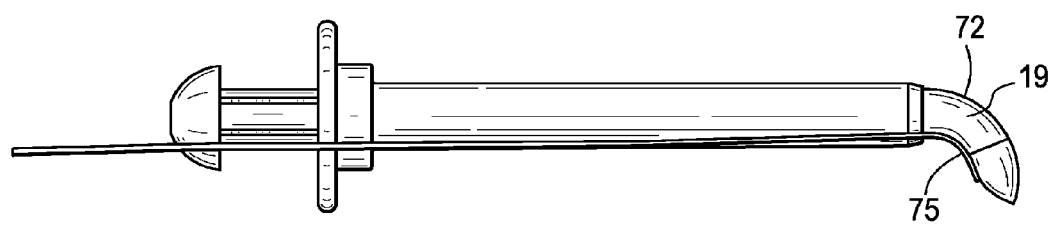
Figure 8D:
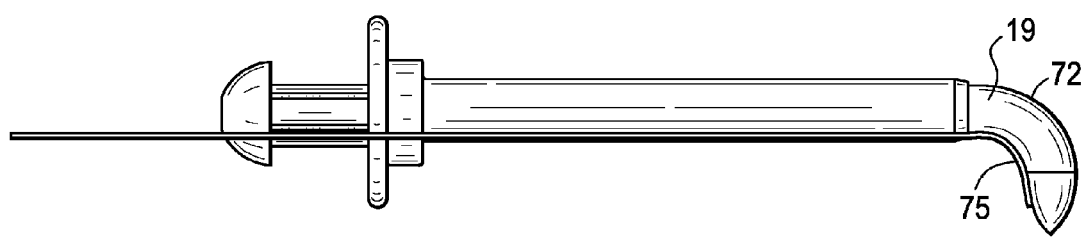

In preferred cases, the sheath is curved to help deliver these curved implants. In cases in which the sheath is curved, the sheath preferably comprises a superelastic shape memory material and has a curved configuration and a straight configuration. The sheath of the insertion device of the present invention also possesses curved sidewalls 71,72, thereby providing for shielded placement of the curved cage in the desired final location prior to sheath retraction. In one type of preferred curved inserter device (FIG. 7C), there is distal loading of the cage, allowing for minimal diameter of the bulleted sheath and cannulated cage holder. The second type of curved inserter device (FIG. 7D) allows for proximal cage loading, but requires an increased diameter of the bulleted sheath and cannulated cage holder. Such a curved inserter can be made to be self-steerable by using a memory metal or memory polymer sheath, or by using a threaded inserter that recovers its unloaded position upon deployment from the docking port.

In some embodiments, and now referring to FIGS. 8A-8D, the cage inserter can be steered into its desired location via cables or other means, wherein the sheath 19 has a tensioning cable 75 attached thereto.

Figure 9:
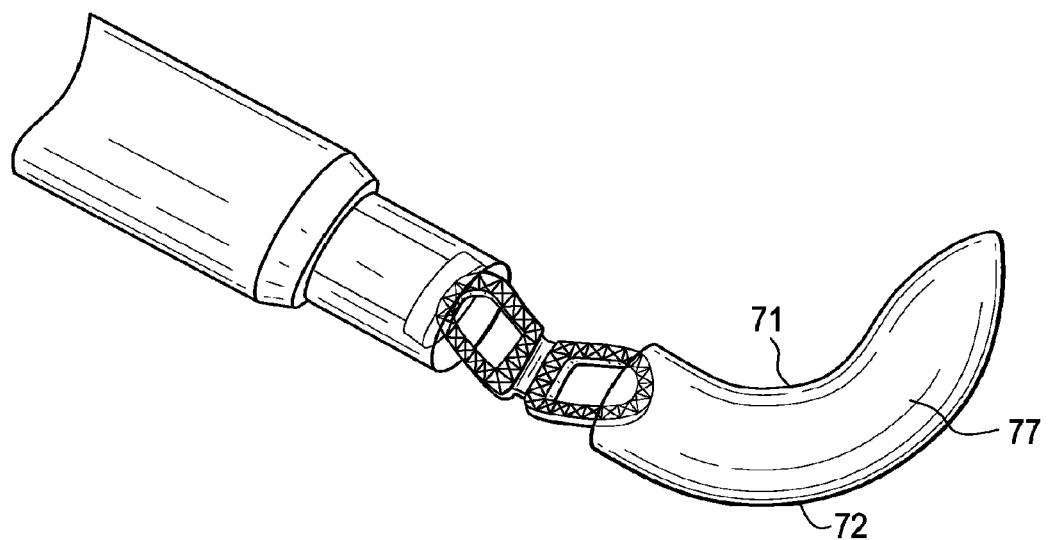
FIG. 9 discloses a distal portion of an inserter of the present invention having a modular expanding sheath tip.

In some embodiments, and now referring to FIG. 9, the cage inserter can have a modular expanding tip 77. The distal tip of the bulleted sheath can be modular and be attached to the proximal portion of the sheath. The modular component can be prepackaged sterile and marketed with the matching cage size contained within to minimize over-distraction. The entire inserter can also be polymeric and/or disposable.

Figure 10A:
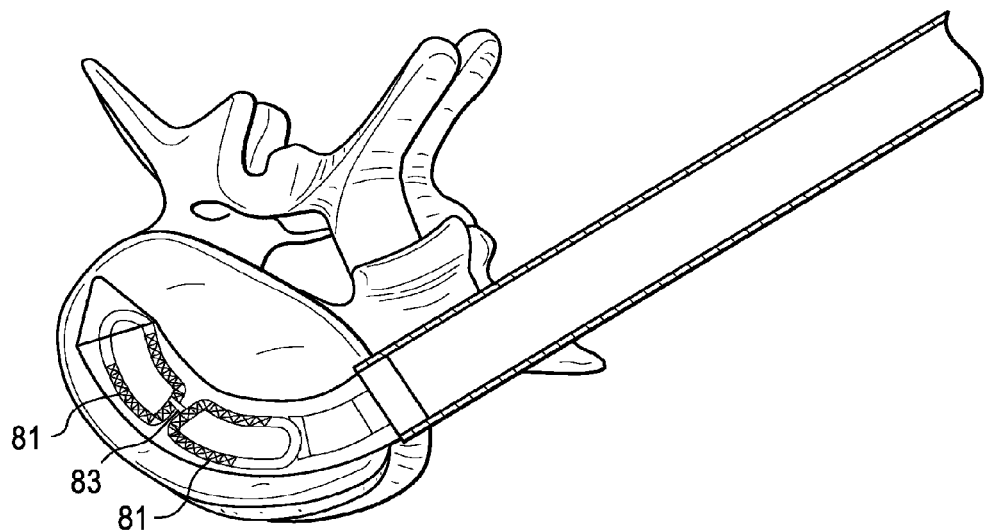
FIGS. 10A-10B disclose the insertion of multi-component cages with the inserter of the present invention.
Figure 10B:
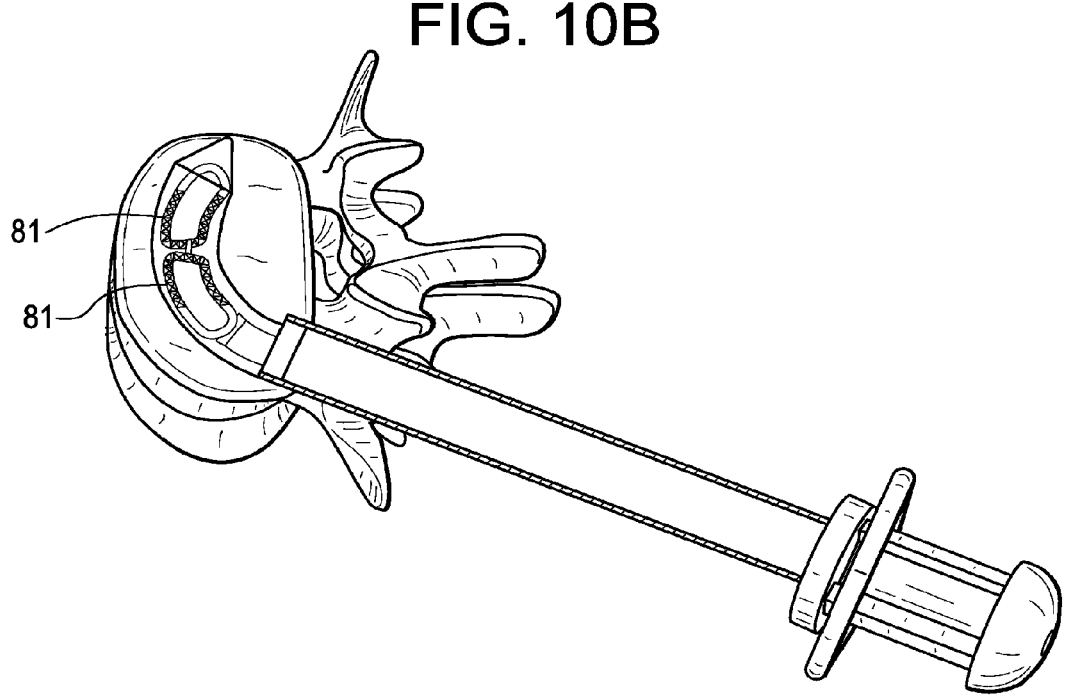

In some embodiments, and now referring to FIGS. 10 A and B, multiple cages 81 may be deployed. A plurality of curved or straight cages (or a combination of curved and straight cages) of a size smaller than a standard cage can be inserted either in succession or simultaneously. In some embodiments thereof, multiple cages can be connected to each other by a cable 83 to provide a more stable construct.

Figure 11A:
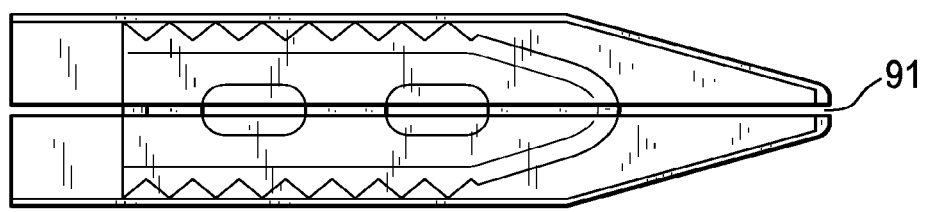
FIGS. 11A-11C disclose a distal portion of an inserter of the present invention fitted with various slit sheaths.
Figure 11B:
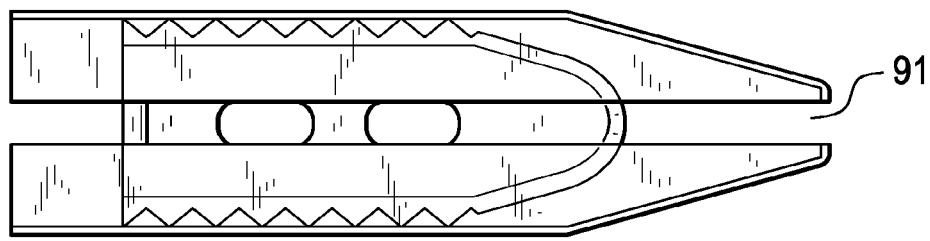
Figure 11C:
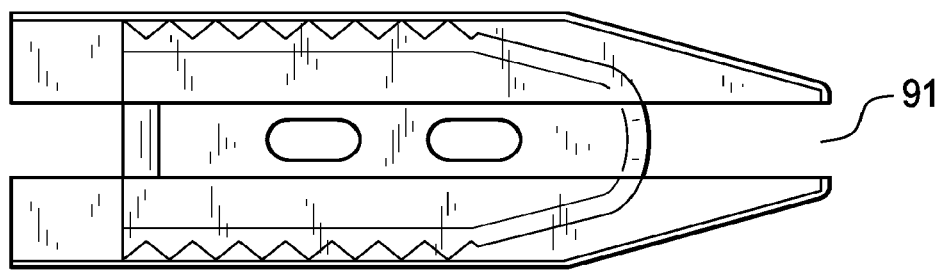

In some embodiments, and now referring to FIGS. 11A-C, the split sheath comprises a longitudinal gap 91 between sheath portions (i.e., the sheath portions do not contact each other). This gap allows for different cage heights to be handled by the same sheath component, thereby reducing the number of potential instruments in the set.

Figure 12A:
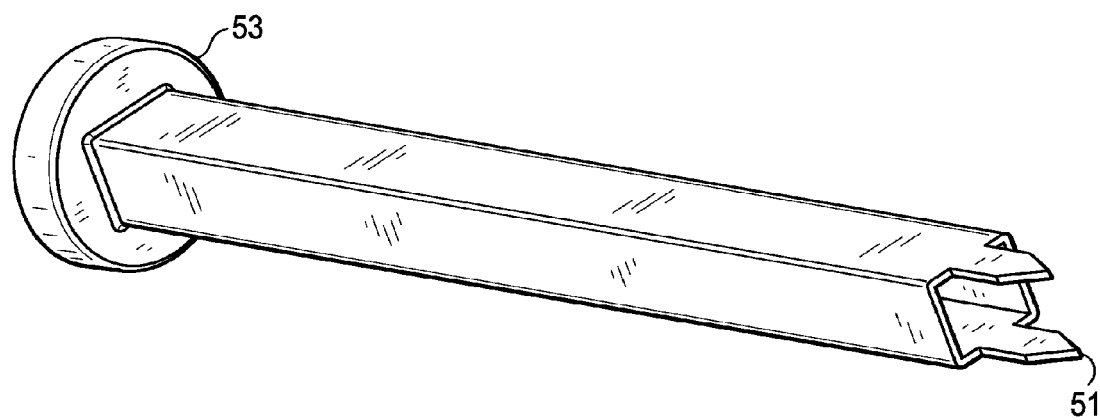
FIG. 12A discloses a docking port component of the present invention having distally extending securement teeth.
Figure 12B:
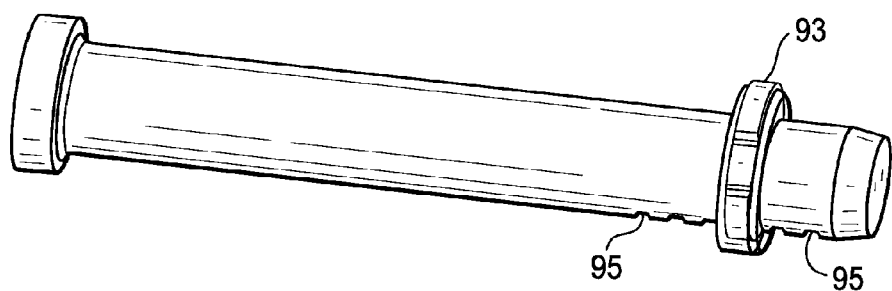
FIG. 12B discloses a docking port component of the present invention having a distally located adjustable collar.

In some embodiments, and now referring to FIGS. 12A-B, the docking port could have multiple means for attachment, such as teeth, to provide security in between or onto the vertebral bodies. In some embodiments, and now referring to FIG. 12A the docking port can have one or more tongs or spikes 51 extending distally from its distal end portion to assist in holding position upon the vertebral bodies or within the disc. Typically, the docking port also has a proximal handle 53.

Now referring to FIG. 12B, the docking port could also include an adjustable collar 93 and incremental adjustment grooves 95. These components could be used to both dock onto the vertebral bodies and control the depth to which the instrument is introduced into the disc space.

Typically, the inserter of the present invention can be made out of any material commonly used in medical instruments. The cage insertion instrument can be made available in a sterile version with preassembled cage and graft, or in a reusable version. If the inserter is designed to be reusable, then it is preferred that all of its components be made of stainless steel. If the inserter is designed to be disposable, then it is preferred that at least some of the components be made of plastic. Preferably, at least one component of the inserter is sterilized. More preferably, each component is sterilized.

The intervertebral fusion cage of the present invention may be manufactured from any biocompatible material commonly used in interbody fusion procedures. In some embodiments, the cage is made from a composite comprising 40-99% polyarylethyl ketone PAEK, and 1-60% carbon fiber. Such a cage is radiolucent. Preferably, the polyarylethyl ketone PAEK is selected from the group consisting of polyetherether ketone PEEK, polyether ketone ketone PEKK, polyether ketone ether ketone ketone PEKEKK, and polyether ketone PEK. Preferably, cage is made from woven, long carbon fiber laminates. Preferably, the PAEK and carbon fiber are homogeneously mixed. Preferably, the composite consists essentially of PAEK and carbon fiber. Preferably, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy Spine, Raynham, Mass., USA. In some embodiments, the composite is PEEK-OPTIMA™, available from Invibio of Greenville, N.C.

In other embodiments, the cage is made from a metal such as titanium alloy, such as Ti-6Al-4V. In other embodiments, the cage is made from an allograft material. In some embodiments, the cage is made from ceramic, preferably a ceramic that can be at least partially resorbed, such as HA or TCP. In other embodiments, the ceramic comprises an oxide such as either alumina or zirconia. In some embodiments, the cage is made from a polymer, preferably a polymer that can be at least partially resorbed, such as PLA or PLG.

In preferred embodiments, the cage is provided in a sterile form.

We claimed:

1. An intervertebral assembly, comprising:
a fusion device having an upper surface, a lower surface disposed such that the upper and lower surfaces are spaced from each other along a vertical direction, an insertion nose, a proximal end portion that is spaced from the insertion nose in a proximal direction that is perpendicular to the vertical direction, and opposed sidewalls that are disposed between the insertion nose and the proximal end portion;
an upper leaf disposed at least partially above the upper surface of the fusion device, the upper leaf having a distal end, wherein the upper leaf is pivotable with respect to the upper surface about a hinge that is offset from the distal end of the upper leaf in the proximal direction;
a lower leaf disposed at least partially below the lower surface, the lower leaf having a distal end, wherein the lower leaf is pivotable with respect to the lower surface about a hinge that is offset from the distal end of the lower leaf in the proximal direction; and
a shaft having a proximal end portion and a distal end portion attached to the proximal end portion of the fusion device;
wherein the intervertebral assembly is movable between a closed arrangement whereby the distal ends of the upper and lower leaves are spaced apart a first distance along the vertical direction, and an open arrangement whereby the distal ends of the upper and lower leaves are spaced apart a second distance greater than the first distance along the vertical direction.

2. The assembly of claim 1, wherein respective inner surfaces of the upper and lower leaves rest against the upper and lower surfaces, respectively, of the fusion device when the intervertebral assembly is in the closed arrangement.

3. The assembly of claim 1, wherein the proximal direction is oriented along a longitudinal direction that further includes a distal direction opposite the proximal direction, the assembly further comprising a threaded member oriented along the longitudinal direction within the fusion device.

4. The assembly of claim 1, wherein the distal end portion of the shaft is threaded, and the fusion device has a threaded hole threadably attached to the shaft.

5. The assembly of claim 4, wherein the threaded hole extends into the proximal end portion of the fusion device.

6. The assembly of claim 1 wherein the proximal direction is oriented along a longitudinal direction that further includes a distal direction that is opposite the proximal direction, the upper and lower leaves each comprises a lateral edge running substantially along the longitudinal direction, and the lateral edges of the upper leaf are substantially parallel with the lateral edges of the lower leaf when the intervertebral assembly is in the closed arrangement.

7. The assembly of claim 1, wherein the distal ends of the upper and lower leaves comprise respective distal tips that tapers towards each other as they extend in a distal direction opposite the proximal direction.

8. The assembly of claim 1, wherein the insertion nose is tapered as it extends in a distal direction opposite the proximal direction.

9. The assembly of claim 1, wherein the fusion device defines a vertical throughhole that extends through the upper and lower surfaces at a location between the side walls.

10. The assembly of claim 1, wherein the hinges are offset from the insertion nose in the proximal direction.

11. The assembly of claim 1, wherein the upper surface defines a plurality of teeth adapted to grip an upper vertebral endplate, and the lower surface defines a plurality of teeth adapted to grip a lower vertebral endplate.

12. An intervertebral assembly, comprising:
a fusion device having an upper surface, a lower surface disposed such that the upper and lower surfaces are spaced from each other along a vertical direction, an insertion nose, a proximal end portion that is configured to attach to a shaft and is spaced from the insertion nose in a proximal direction that is perpendicular to the vertical direction, and opposed sidewalls that are disposed between the insertion nose and the proximal end portion;
a plurality of leaves each having a respective distal end, wherein each of the leaves is pivotable with respect to the fusion device about a hinge that is offset from the respective distal end in the proximal direction;
wherein the intervertebral assembly is movable between a closed arrangement whereby the respective distal ends of an opposed pair of the plurality of leaves are spaced apart a first distance along the vertical direction, and an open arrangement whereby the respective distal ends of the opposed pair of the plurality of leaves are spaced apart a second distance greater than the first distance along the vertical direction,
wherein when the intervertebral assembly is in the closed arrangement, the opposed pair of the leaves surround the upper and lower surfaces of the fusion device.

13. The assembly of claim 12, further comprising a shaft having a proximal end portion and a distal end portion spaced from the proximal end portion along a distal direction that is opposite the proximal direction, the distal end portion configured to attach to the proximal end portion of the fusion device.

14. The assembly of claim 13, wherein the distal end portion of the shaft is attached to the proximal end portion of the fusion device.

15. The assembly of claim 14, wherein the distal end portion of the shaft is threadably attached to the proximal end portion of the fusion device.

16. The assembly of claim 14, wherein the distal end portion of the shaft is configured to threadably attach to the proximal end portion of the fusion device.

17. The assembly of claim 12, wherein the fusion device defines a vertical throughhole that extends through the upper and lower surfaces at a location between the side walls.

18. The assembly of claim 12, wherein the upper surface defines a plurality of teeth adapted to grip an upper vertebral endplate, and the lower surface defines a plurality of teeth adapted to grip a lower vertebral endplate.

19. The assembly of claim 12, wherein respective surfaces of the opposed pair of the plurality of leaves are substantially parallel to each other when the intervertebral assembly is in the closed arrangement.

20. The assembly of claim 12, wherein respective inner surfaces of the upper and lower leaves rest against the upper and lower surfaces, respectively, of the fusion device when the intervertebral assembly is in the closed arrangement.

* * * * *